United States Patent [19]

Diamond et al.

[11] Patent Number: 5,288,854
[45] Date of Patent: Feb. 22, 1994

[54] FUNCTIONAL DERIVATIVES OF ICAM-1 WHICH ARE SUBSTANTIALLY CAPABLE OF BINDING TO LFA-1 BUT ARE SUBSTANTIALLY INCAPABLE OF BINDING TO MAC-1

[75] Inventors: Michael S. Diamond, Cambridge; Donald E. Staunton, Chestnut Hill; Timothy A. Springer, Newton, all of Mass.

[73] Assignee: Center For Blood Research, Inc., Boston, Mass.

[21] Appl. No.: 618,286

[22] Filed: Nov. 28, 1990

[51] Int. Cl.$^5$ .......................... C07K 9/00; A61K 37/02
[52] U.S. Cl. .................................. 530/395; 530/350; 530/808; 530/827; 530/868; 424/88
[58] Field of Search ................. 530/350, 395, 402–403, 530/808, 827, 868; 424/88; 514/2, 12, 8, 885

[56] References Cited

PUBLICATIONS

Sanchez-Madrid, F. et al. J. Exp. Med. 158:1785–1803. Dec. 1983. "A human leukocyte ...".
Sanchez-Madrid, F. et al. J. Exp. Med. 158:586–602. Aug. 1983. "Mapping of antigenic ...".
Staunton, D. et al. Cell 52:925–933. Mar. 1988. "Primary Structure of ICAM-1 ...".
Altieri, D. C. et al., *J. Biol. Chem.* 263:7007–7015 (1988).
Altieri, D. C. et al., *J. Cell. Biol.* 107:1893–1900 (1988).
Arnaout, M. A. et al., *J. Clin. Invest.* 74:1291–1300 (1984).
Arnaout, M. A., et al., *J. Cell. Physiol.* 137:305–309 (1988).
Anderson, D. C., et al., *Ann. Rev. Med.* 38:175–194 (1987).
Anderson, D. C. et al., *J. Immunol.* 137:15–27 (1986).
Beller, D. I., et al., *J. Exper. Med.* 156:1000–1009 (1982).
Bullock, W. D., et al., *J. Exper. Med.* 165:195–210 (1987).
Dana, N. et al., *J. Immunol.* 137:3259–3263 (1986).
Davignon, D., et al., *J. Immunol.* 127:590–595 (1981).
Davignon, D., et al., *PNAS U.S.A.* 78:4535–4539 (1981).
Detmers, P. A. et al., *J. Cell. Biol.* 105:1137–1145 (1987).
Dustin, M. L., et al., *J. Cell. Biol.* 107:321–331 (1988).
Hogg, N., et al., *Eur. J. Immunol.* 16:240–248 (1986).
Hynes, R. O., *Cell* 48:549–554 (1987).
Caligaris-Cappio, F., et al., *Blood* 66:1035–1042 (1985).
Keizer, G. D., et al., *J. Immunol.* 138:3130–3136 (1987).
Keizer, G. D., et al., *Eur. J. Immunol.* 17:1317–1322 (1987).
Kishimoto, T. K., et al., *Cell* 48:681–690 (1987).
Kishimoto, T. K., et al., *Adv. Immunol.* 46:149–182 (1989).
Krensky, A. M., et al., *J. Immunol.* 131:611–616 (1983).
Lanier, L. L., et al., *Eur. J. Immunol.* 15:713–718 (1985).
Lo., S. K., et al., *J. Immunol.* 143(10):3325–3329 (1989).
Lo, S. K., et al., *J. Exp. Med.* 169:1779–1793 (1989).
Luscinskas, F. W., et al., *J. Immunol.* 142(7):2257–2263 (1989).
Marlin, S. D., *Cell* 51:813–819 (1987).
Mentzer, S. J., et al., *J. Cell. Physiol.* 130:410–415 (1987).
Micklem, K. J., et al., *Biochem. J.* 231:233–236 (1985).

(List continued on next page.)

*Primary Examiner*—Christine M. Nucker
*Assistant Examiner*—T. Cunningham
*Attorney, Agent, or Firm*—Sterne, Kessler, Goldstein & Fox

[57] ABSTRACT

The present invention is directed to functional derivatives of ICAM-1 which are substantially capable of binding to LFA-1 but are substantially incapable of binding to MAC-1. Such functional derivatives of ICAM-1 contain an addition to, a substitution of, or an insertion of one or more amino acids within domain 3 of ICAM-1.

5 Claims, 6 Drawing Sheets

PUBLICATIONS

Miller, L. J., et al., *J. Immunol.* 138:2381–2383 (1987).
Miller, L. J., et al., *J. Immunol.* 137:2891–2900 (1986).
Miller, L. J., et al., *J. Clin. Invest.* 80:535–544 (1987).
Mosser, D. M., et al., *J. Immunol.* 135:2785–2789 (1985).
Rosen, H., et al., *J. Exper. Med.* 166:1685–1701 (1987).
Ruoslahti, E., et al., *Science* 238:491–497 (1987).
Sanchez-Madrid, F., et al., *PNAS U.S.A.* 79:7489–7493 (1982).
Sastre, L., et al., *PNAS U.S.A.* 83:5644–5648 (1986).
Schwarting, R., et al., *Blood* 65:974–983 (1985).
Simmons, D., et al., *Nature* 331:624–627 (1988).
Smith, C. W., et al., *J. Clin. Invest.* 83:2008–2017 (1989).
Springer, T. A., et al., *Ann. Rev. Immunol.* 5:223–252 (1987).
Springer, T. A., et al., *Eur. J. Immunol.* 9:301–306 (1979).
Springer, T. A., et al., *Nature* 314:540–542 (1985).
Springer, T. A., et al., *Fed. Proc.* 44:2660–2663 (1985).
Staunton, D. E., *Nature* 339:61–64 (1989).
Staunton, D. E., et al., *Cell* 61:243–254 (1990).
te Velde, A. A., et al., *Immunology* 61:261–267 (1987).
Todd, R. F., et al., *Hem. Onc. Clinics N.A.* 2:13–31 (1988).
Todd, R. F., et al., *J. Clin. Invest.* 74:1280–1290 (1984).
Vedder, N. B., et al., *J. Clin. Invest.* 81:676–682 (1988).
Wright, S. D., et al., *PNAS U.S.A.* 85:7734–7738 (1988).
Yancey, K. B., et al., *J. Immunol.* 135:465–470 (1985).

MAPSSPRPALPALLVLLGALFPGPGNAQTSVSPSKVILPRGGSVLVTCSTSCDQPKLLGIE

TPLPKKELLLPGNNRKVYELSNVQEDSQPMCYSNCPDGQSTAKTFLTVYWTPERVELA

PLPSWQPVGKNLTLRCQVEGGAPRANLTVVLLRGEKELKREPAVGEPAEVTTTVLVRR

DHHGANFSCRTELDLRPQGLELFENTSAPYQLQTFVLPATPPQLVSPRVLEVDTQGTVV

CSLDGLFPVSEAQVHLALGDQRLNPTVTYGNDSFSAKASVSVTAEDEGTQRLTCAVILG

NQSQETLQTVTIYSFPAPNVILTKPEVSEGTEVTVKCEAHPRAKVTLNGVPAQPLGPRA

QLLLKATPEDNGRSFSCSATLEVAGQLIHKNQTRELRVLYGPRLDERDCPGNWTWPEN

SQQTPMCQAWGNPLPELKCLKDGTFPLPIGESVTVTRDLEGTYLCRARSTQGEVTREVT

VNVLSPRYEIVIITVVAAAVIMGTAGLSTYLNRQRKIKKYRLQQAQKGTPMKPNTQATPP (SEQ. ID. No. 1)

Fig. 10

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 532 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
Met Ala Pro Ser Ser Pro Arg Pro Ala Leu Pro Ala Leu Leu Val Leu
 1               5                  10                  15
```

```
Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
        50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
            165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
            245                 250                 255

Gln Arg Leu Asn Pro Thr Val Thr Tyr Gly Asn Asp Ser Phe Ser Ala
        260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
            325                 330                 335

Arg Ala Lys Val Thr Leu Asn Gly Val Pro Ala Gln Pro Leu Gly Pro
        340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
            405                 410                 415

Pro Met Cys Gln Ala Trp Gly Asn Pro Leu Pro Glu Leu Lys Cys Leu
        420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
```

|   |   |   |   |   |   |   |   |   |   |   |   |   |   |   |
|---|---|---|---|---|---|---|---|---|---|---|---|---|---|---|
|   |   |   | 450 |   |   |   | 455 |   |   |   |   | 460 |   |   |
| Glu | Val | Thr | Arg | Glu | Val | Thr | Val | Asn | Val | Leu | Ser | Pro | Arg | Tyr | Glu |
| 465 |   |   |   |   | 470 |   |   |   |   | 475 |   |   |   |   | 480 |
| Ile | Val | Ile | Ile | Thr | Val | Val | Ala | Ala | Ala | Val | Ile | Met | Gly | Thr | Ala |
|   |   |   |   | 485 |   |   |   |   | 490 |   |   |   |   | 495 |   |
| Gly | Leu | Ser | Thr | Tyr | Leu | Tyr | Asn | Arg | Gln | Arg | Lys | Ile | Lys | Lys | Tyr |
|   |   |   | 500 |   |   |   |   | 505 |   |   |   |   | 510 |   |   |
| Arg | Leu | Gln | Gln | Ala | Gln | Lys | Gly | Thr | Pro | Met | Lys | Pro | Asn | Thr | Gln |
|   |   |   | 515 |   |   |   | 520 |   |   |   |   | 525 |   |   |   |
| Ala | Thr | Pro | Pro |   |   |   |   |   |   |   |   |   |   |   |   |
|   | 530 |   |   |   |   |   |   |   |   |   |   |   |   |   |   |

FUNCTIONAL DERIVATIVES OF ICAM-1 WHICH ARE SUBSTANTIALLY CAPABLE OF BINDING TO LFA-1 BUT ARE SUBSTANTIALLY INCAPABLE OF BINDING TO MAC-1

This invention was made in part with government support. The government has certain rights in this invention.

FIELD OF THE INVENTION

The present invention relates to the intercellular adhesion molecule, ICAM-1, and its ability to bind to the leukocyte adhesion receptor Mac-1. The invention further pertains to the use of the ICAM-1 - Mac-1 binding ability to treat inflammation.

DESCRIPTION OF THE RELATED ART

I. Cellular Adhesion

The immune system is responsible for protecting an animal from foreign invaders, such as bacteria, viruses, etc. An excellent review of the defense system is provided by Eisen, H. W. (In: *Microbiology*, 3rd Ed., Harper & Row, Philadelphia, PA (1980), pp. 290-295 and 381-418). The ability of the immune system to protect an animal against foreign invaders depends, in large measure, on the presence and function of blood cells known an leukocytes.

A primary event in the immune system's response to infectious agents is the recruitment of circulating neutrophils to the inflammatory site. Adhesion to the endothelium is the prerequisite physical step for extravasation to the peripheral site of injury. Neutrophil localization has been examined on a molecular level to define both the sequence of events that promote neutrophil exit from the bloodstream and the cognate proteins on the surface of neutrophils and the endothelial cells that coordinate this interaction.

The ability of leukocytes to protect an animal or human has been found to require the adhesion of immune system cells to cellular and extracellular substrates. For example, leukocytes must be able to attach to endothelial cells so that they can migrate from the circulation to sites of ongoing inflammation. Furthermore, they must attach to antigen-presenting cells so that a normal immune response can occur. They must also be able to attach to appropriate target cells so that the lysis of virally-infected (or tumor) cells can occur. Furthermore, leukocytes must be able to attach to various activated proteins (such as iC3b—the activated form of the third component of complement) so that they may efficiently phagocytose and clear microbial and cellular debris. Thus, leukocyte adhesion is a requisite of a normally functioning host defense system The inhibition of this defense system is desirable in cases such as transplantation, because the host "sees" the transplanted tissue as foreign and initiates an immune response to that tissue. Leukocyte adhesion is, therefore, also involved in the rejection of transplanted tissue and organs. Thus, an understanding of leukocyte adhesion may enable one to either augment an animal's ability to fight infection or suppress an animal's capacity to reject transplanted tissue.

Leukocyte surface molecules involved in mediating leukocyte adhesion were identified using hybridoma technology. Briefly, monoclonal antibodies directed against human T-cells (Davignon, D., et al., *Proc. Natl Acad. Sci. USA* 78:4535-4539 (1981)) and mouse spleen cells (Springer, T., et al., *Eur. J. Immunol.* 9:301-306 (1979)) were identified which bound to leukocyte surfaces and inhibited the attachment-related functions described above (Springer, T., et al., *Fed. Proc.* 44:2660-2663 (1985)). The molecules which were recognized by these antibodies comprise a set of leukocyte adhesion receptors known as the "Lymphocyte Function-Associated Antigen-1 family" (or the "LFA-1 family") of adhesion receptor molecules.

The LFA-1 family of adhesion receptor molecules contains three highly related cell surface glycoproteins: "LFA-1" (CD11a/CD18), "Mac-1" (CD11b/CD18), and "p150,95" (CD11c/CD18). These glycoproteins are members of a family of proteins, the leukocyte integrins, that are critical for adhesive functions in the immune system Springer et al. (*Ann. Rev. Immunol*, 5:223-252, (1987)).

Whereas LFA-1 is found on the surfaces of most leukocytes (Springer, T. A., et al., *Immunol. Rev.* 68:111-135 (1982)), Mac-1 and p150,95 are found primarily on macrophages, granulocytes and other large granular lymphocytes (Springer, T. A., et al., *Immunol. Rev.* 68:111-135 (1982); Keizer, G., et al., *Eur. J. Immunol.* 15:1142-1147 (1985)).

The LFA-1 family of adhesion receptor proteins are heterodimers which possess a common $\beta$ chain that is non-covalently associated with unique $\alpha$ chains. The alpha-subunits of the family have been found to differ from one another and are designated CD11a, CD11b, and CD11c, respectively. The glycosylated alpha-subunits have approximate molecular weights of 175, 160, and 150 kd, respectively. In contrast, the beta-subunit of the LFA-1 family of adhesion receptors (designated "CD18") has been found to be identical, and to have a molecular weight of 95 kd (Sanchez-Madrid, F., et al., *J. Exper. Med.* 158:1785-1803 (1983); Keizer, G. D., et al, *Eur. J. Immunol.* 15:1142-1147 (1985); Springer, T., *Fed. Proc.* 44:2660-2663 (1985); Sanchez-Madrid, F., et al., *J. Exper. Med.* 158:586-602 (1983)).

Although the alpha-subunits of the glycoproteins do not exhibit the extensive homology shared by the beta-subunits, close analysis has revealed that there are substantial similarities between them. Reviews of the similarities between the alpha and beta-subunits of the adhesion molecule glycoprotein family are provided by Sanchez-Madrid, F., et al. (*J. Exper. Med.* 158:586-602 (1983); *J. Exper. Med.* 158:1785-1803 (1983); Miller, L. J., et al., *J. Immunol.* 138:2381-2383 (1987)).

The importance of the LFA-1 family of receptors was initially recognized in studies which showed the ability of monoclonal antibodies (which were capable of binding to either the specific alpha-subunits, or the common beta-subunit) to inhibit adhesion-dependent leukocyte functions (Sanchez-Madrid, F., et al., *Proc. Natl. Acad. Sci. USA* 79:7489-7493 (1982); Beller, D. I., et al., *J. Exper. Med.* 156:1000-1009 (1982)).

The importance of the leukocyte integrins was confirmed by the discovery of a clinical syndrome, "Leukocyte Adhesion Deficiency" syndrome ("LAD"), that is characterized by a congenital deficiency or absence of the common $\beta$ (CD18) chain and presents with diminished pus formation, abnormal wound healing, and grave susceptibility to pyrogenic infections (Anderson, D. C., et al., *Fed. Proc.* 44:2671-2677 (1985); Anderson, D. C., et al., *J. Inf. Dis.* 152:668-689 (1985); Anderson, D. C., et al.. *Ann. Rev. Med.* 38:175-194 (1987); Amaout, M. A., et al., *J. Clin. Invest.* 74:1291-1300 (1984)) as well as abnormalities of adhesion-dependent leukocyte functions in vitro (Anderson, D. C., et al., *Ann. Rev. Med.* 38:175-194 (1987); Todd, R. F., et al., *Hem. Onc. Clinics N. A.* 2:13-31 (1988)).

Leukocytes from LAD patients display in vitro defects which were similar to those observed when leukocytes of normal individuals were antagonized by antibody specific for members of the LFA-1 family. LAD patients were found to be unable to mount a normal immune response. This failure was found to be due to an inability of the leukocytes of LAD patients to adhere to cellular and extracellular substrates (Anderson, D. C., et al.. *Fed. Proc.* 44:2671-2677 (1985); Anderson, D. C., et al.. *J. Infect. Dis.* 152:668-689 (1985)). These studies show that inflammatory reactions are mitigated when leukocytes are unable to adhere in a normal fashion due to the lack of functional adhesion molecules on their cell surface.

II. The Nature of the Leukocyte Adhesion Proteins of the LFA-1 Family

The three leukocyte adhesion proteins Mac-1, p150,95, and LFA-1 differ in function and in expression on leukocyte subpopulations. Mac-1 and p150,95 are expressed on neutrophils, and monocytes (Springer, T. A., et al., In: *Biochemistry of Macrophages* (CIBA Symposium 118); Pitman, London, pp. 102-126 (1986)). During differentiation of blood monocytes into tissue macrophages, expression of p150,95 is greatly increased and Mac-1 expression is decreased (Schwarting, R., et al., *Blood* 65:974-983 (1985); Hogg, N., et al., *Eur. J. Immunol* 16:240-248 (1986)). p150,95 is also expressed on certain types of activated T and B lymphocytes, but is not expressed on these cells in the blood (Kaligaris-Cappio, F., et al., *Blood* 66:1035-1042 (1985); Miller, L. J., et al., *J. Immunol.* 137:2891-2900 (1986); Keizer, G. D., et al., *J. Immunol.* 138:3130-3136 (1987)).

LFA-1 is present on all leukocytes except a subset of macrophages. Monoclonal antibody blocking studies have shown that LFA-1 is important in T-lymphocyte-mediated killing, T helper lymphocyte responses, natural killing, and antibody-dependent killing (Springer, T. A., et al., *Ann. Rev. Immunol* 5:223-252 (1987)). Adhesion to the target cell is a step which is blocked by antibodies against LFA-1. Functional studies have suggested that LFA-1 interacts with several ligands, one of which is ICAM-1 (Rothlein, R., et al., *J. Immunol.* 137:1270-1274 (1986)).

Mac-1 and p150,95 are expressed in an intracellular, vesicular compartment in circulating neutrophils and monocytes which is mobilized to the cell surface by inflammatory mediators (Todd, R. F., et al., *J. Clin. Invest.* 74:1280-1290 (1984); Springer, T. A., et al., In: *Biochemistry of Macrophages* (CIBA Symposium 118), Pitman, London, pp. 102-126 (1986); Lanier, L. L., et al., *Eur. J. Immunol.* 15:713-718 (1985); Yancey, K. B., et al.. *J. Immunol.* 135:465-470 (1985). This mobilization correlates with increased adhesiveness (Anderson, D. C., et al., *Ann. Rev. Med.* 38:175-194 (1987)). Mac-1 α-subunit message was detected in blood monocytes and PMA-induced myeloid cell lines, but not in cells of the T or B lineages, correlating with Mac-1 protein surface expression.

Some cytotoxic T lymphocyte clones have been found to express similar quantities of p150,95 and LFA-1. Monoclonal antibodies to the LFA-1 and p150,95 alpha-subunits inhibit killing by such CTL clones to similar extents and are additive in their inhibitory effects (Keizer, G. D., et al., *J. Immunol.* 138:3130-3136 (1987)). Furthermore, antibodies to p150,95 alpha-subunits have been shown to inhibit monocyte attachment to endothelium (Keizer, G. D., et al., *Eur. J. Immunol.* 17:1317-1322 (1987)).

Monoclonal antibodies to Mac-1 or p150,95 inhibit neutrophil aggregation and adherence to endothelial cells, protein-coated surfaces, bacteria, protozoan parasites, and fungi (Harlan, J. M., et al., *Blood* 66:167-178 (1985); Springer, T. A., et al., In: *Biochemistry of Macrophages* (CIBA Symposium 118), pitman, London, pp. 102-126 (1986); Dana, N., et al., *J. Immunol.* 137:3259 (1986); Bullock, W. D., et al., *J. Exper. Med.* 165:195-210 (1987); Mosser, D. M., et al., *J. Immunol.* 135:2785-2789 (1985)).

MAC-1 (CD11b/CD18) is a leukocyte adhesion glycoprotein that has been demonstrated to bind multiple ligands including iC3b (Beller, D. I. et al., *J. Exper. Med.* 156:1000-1009 (1982)), fibrinogen (Altieri, D. C. et al., *J. Cell. Biol.* 107:1893-1900 (1988); Wright, S. D. et al., *Proc. Nat'l. Acad. Sci. (U.S.A.)* 85:7734-7738 (1988)),and Factor X (Altieri, D. C. et al.; *J. Biol. Chem.* 863:7007-7015 (1988)) in addition to its role in cell-cell and cell-substrate adhesive interactions. Detergent-soluble Mac-1 and p150,95 have been shown to be able to bind to iC3b-Sepharose (Micklem, K. J., et al., *Biochem. J.* 231:233-236 (1985)).

The α-subunit of Mac-1 is a transmembrane protein of 1137 residues with a long extracellular domain (1092 residues) and a 19-amino acid cytoplasmic tail. The extracellular domain contains 3 putative divalent cation-binding sequences and 19 potential N-glycosylation sites. The amino acid sequence of Mac-1 α shows that it is a member of the integrin superfamily; Mac-1 α shows 63% identity to the α-subunit of the leukocyte adhesion glycoprotein p150,95 and 25% to the α-subunits of the extracellular matrix receptors platelet glycoprotein IIb/IIIa, the fibronectin receptor and the vitronectin receptor The Mac-1 α-subunit putative divalent cation-binding sites and the flanking regions exhibit a high degree of identity both to the p150,95 α-subunit (87% identity at the amino acid level) and to the rest of the integrin α-subunits (38%). The α-subunit of Mac-1, like the p150,95 α-subunit, contains a domain of 187 amino acids in the extracellular region which is absent in other integrins. This inserted or "I" domain is homologous to the A domains of van Willebrand factor, which in turn are homologous to regions of the C3-binding proteins factor B and C2. These findings draw attention to this region of Mac-1 as a potential binding site for iC3b.

The functional role of Mac-1 was first illustrated by the ability of anti-Mac-1 α-subunit monoclonal antibodies (MAb) to block the rosetting of iC3b-coated erythrocytes to macrophages and polymorphonuclear leukocytes (Beller, D. I. et al., *J. Exper. Med.* 156:1000-1009 (1982)), demonstrating that Mac-1 is indistinguishable from the complement receptor type three (CR3). Subsequently, the involvement of Mac-1 in inflammatory processes was evidenced by the inhibition of neutrophil aggregation and adhesion to endothelial cells by anti-Mac-1 α-subunit and anti-b-subunit-specific MAb (Anderson, D. C. et al., *J. Immunol.* 137:15-27 (1986); Dana, N. et al., *J. Immunol.* 137:3259-3263 (1986); Vedder, N. B. et al., *J. Clin. Invest.* 81:672-682 (1988)). Recent epitope mapping studies have suggested that the sites involved in iC3b-binding are distinct from those involved in neutrophil aggregation and adherence to protein-coated plastic (Anderson, D. C. et al., J.

*Immunol.* 137:15-27 (1986); Dana, N. et al., *J. Immunol.* 137:3259-3263 (1986), Rosen, H. et al.. *J. Exper. Med.* 166:1685-1701 (1987)). Therefore, Mac-1 appears to be a multivalent receptor with at least two independent adhesion-related functions.

The expression of functional activity of Mac-1 is regulated during leukocyte differentiation and activation. Differentiation and maturation of myelomonocytic cell lines results in increased Mac-1 expression (Miller, L. J. et al., *J. Immunol.* 137:2891-2900 (1986)), while blood monoctye differentiation into tissue macrophages is accompanied by a considerable decrease in the amount of Mac-1 on all cell surface (Hogg, N. et al., *Eur. J. Immunol.* 16:240-248 (1986)). The expression of Mac-1 on the surface of circulating neutrophils and monocytes is upregulated by inflammatory stimuli; Mac-1 is stored in an intracellular vesicular compartment which is rapidly mobilized to the cell surface by chemoattractants (Todd, R. F. et al., *J. Clin. Invest.* 74:1280-1290 (1984)); Miller, L. J. et al., *J. Clin. Invest.* 80:535-544 (1987)). Although the augmented expression of Mac-1 can lead to increased adhesiveness, qualitative changes after cell activation may also be important in regulation ligand binding (Detmers, P. A. et al., *J. Cell Biol.* 105:1137-1145 (1987)). Both the qualitative and quantitative changes may be important in regulation of leukocyte binding to post-capillary endothelium at inflammatory sites.

The N-terminal sequence of the murine and human Mac-1 α-subunits (Miller, L. J. et al., *J. Immunol.* 138:2381-2383 (1987); Springer, T. A. et al., *Nature* 314:540-542 (1985)) and a murine genomic clone encoding a short N-terminal exon (Sastre, L. et al., *Proc. Natl. Acad. Sci. (U.S.A.)* 83:5644-5648 (1986)) have been reported.

Thus, in summary, the ability of leukocytes to maintain the health and viability of an animal requires that they be capable of adhering to other cells (such as endothelial cells) and proteins (such as iC3b). This adherence has been found to require contacts which involve specific receptor molecules present on the leukocyte surface of the leukocytes. These cell surface receptor molecules have been found to be highly related to one another. Humans whose leukocytes lack these cell surface receptor molecules exhibit chronic and recurring infections, as well as other clinical symptoms.

Since leukocyte adhesion is involved in the process through which foreign tissue is identified and rejected, an understanding of this process is of significant value in the fields of organ transplantation, tissue grafts, allergy and oncology.

SUMMARY OF THE INVENTION

The present invention relates to the cellular adhesion molecule, ICAM-1, and to the leukocyte cell surface adhesion receptor molecule Mac-1, and in particular, to the identification of the Mac-1 binding site on ICAM-1. The knowledge of the sequence and structure of this binding site facilitates the use of Mac-1 and ICAM-1 functional derivatives in the treatment of inflammation.

Previous studies with domain deletion and amino acid substitution mutants of ICAM-1 have localized the LFA-1 and human rhinovirus binding sites to the first $NH_2$-terminal Ig-like domain (Staunton, D. E., et al., *Cell* 61:243-254 (1990)). The leukocyte integrin Mac-1, which is closely related to LFA-1, has also been shown to bind ICAM-1 (Smith, C. W., et al., *J. Clin. Invest.* 83:2008-2017 (1989)).

The present invention derives, in part, from a localization of the Mac-1 binding site on ICAM-1. Unexpectedly, a distinct binding region was found in the third $NH_2$-terminal Ig-like domain, and that two glycosylation sites in this domain dramatically altered the ability of ICAM-1 to adhere to Mac-1.

In detail, the invention pertains to an ICAM-1 functional derivative, especially a soluble functional derivative, which is substantially incapable of binding to Mac-1, but is substantially capable of binding to LFA-1.

The invention specifically includes those of the above-described ICAM-1 functional derivatives which comprises Domains 1, 2, 3 and 4 of ICAM-1, and especially such derivatives which contain a mutation in Domain 3 of ICAM-1. Particularly preferred mutations in Domain 3 are mutations in ICAM-1 residues 229-231, or 254-256 of ICAM-1.

The present invention also provides an ICAM-1 functional derivative, especially a soluble derivative, which is substantially incapable of binding to LFA-1, but is substantially capable of binding to Mac-1. Among such derivatives are those which lack Domain 1, of ICAM-1, and those which contain Domains 1, 2, 3, 4 and 5 of ICAM-1, but contain a mutation in Domains 1 or 2 of ICAM-1. Particularly preferred mutations are those in ICAM-1 residue(s) E34, Q58ED, or Q73 of Domain 1 of ICAM-1. Among preferred ICAM-1 functional derivatives which lack Domain 1 are those comprising Domains 3 and 4 of ICAM-1.

The invention also provides an ICAM-1 functional derivative which is substantially incapable of binding to Mac-1 and LFA-1, but is substantially capable of binding a human rhinovirus.

The invention also pertains to an ICAM-1 functional derivative lacking a glycosylation site, wherein the derivative is capable of enhanced binding ability to Mac-1. Most preferred for this purpose is the loss of a glycosylation site at ICAM-1 residue N269, N240 or N358 of ICAM-1.

The invention also provides an anti-inflammatory agent characterized in being capable of treating inflammation caused by a reaction of the non-specific defense system, but being substantially incapable of suppressing inflammation caused by a reaction of the specific defense system.

In particular, the invention provides an anti-inflammatory agent which is an ICAM-1 functional derivative, especially a soluble derivative, that is substantially incapable of binding to LFA-1, but is substantially capable of binding to Mac-1.

The invention also provides an anti-inflammatory agent characterized in being capable of treating inflammation caused by a reaction of the specific defense system, but being substantially incapable of suppressing inflammation caused by a reaction of the non-specific defense system.

In particular, the invention provides an anti-inflammatory agent which is an ICAM-1 functional derivative, especially a soluble derivative, that is substantially incapable of binding to Mac-1, but is substantially capable of binding to LFA-1.

BRIEF DESCRIPTION OF THE FIGURES

FIG. 10 shows the amino acid sequence of ICAM-1.

DESCRIPTION OF THE PREFERRED EMBODIMENTS

I. Treatment of Inflammation

Figure 1:
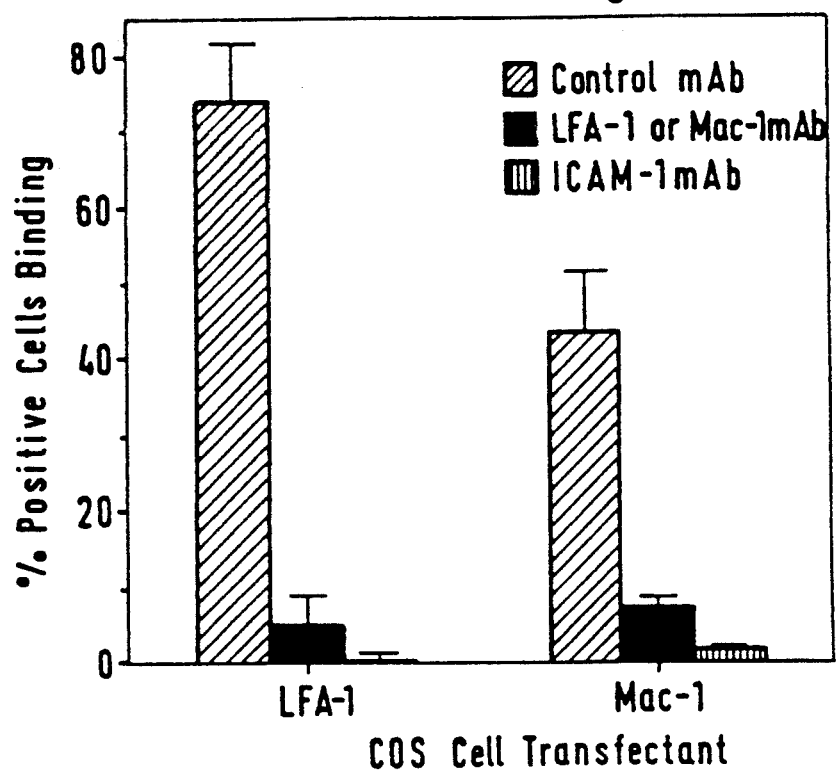
FIG. 1 shows the adhesion of LFA-1 and Mac-1 COS cell transformants to purified ICAM-1.

The present invention pertains to ICAM-1, Mac-1 and their "functional derivatives," and to antibodies (and antibody fragments) which are capable of binding to ICAM-1 and thereby affecting the ability of ICAM-1 to bind to Mac-1.

One aspect of the present invention relates to the discovery that ICAM-1 is capable of binding to Mac-1, and to the identification of the domains of ICAM-1 which are responsible for the molecule's ability to bind to Mac-1. These discoveries permit the production of functional derivatives of ICAM-1 capable of binding to the Mac-1 heterodimer, alpha- or beta subunits. Similarly, they permit the production of functional derivatives of the Mac-1 heterodimer, alpha- or beta subunits which are capable of binding to ICAM-1.

The adhesion ability of circulating neutrophils and monocytes results from interactions involving the Mac-1 receptor molecule. Since cellular adhesion is required in order that such cells may migrate to sites of inflammation and/or carry out various effector functions contributing to inflammation, agents which inhibit such cellular adhesion will attenuate or prevent inflammation. The Mac-1 receptor molecule is present on the surface of neutrophils and monocyte cells. The adhesion of these cells to plastic surfaces, or to monolayers of endothelial cells, is mediated by the Mac-1 receptor molecule. In addition, the ability of monocytes to phagocytose foreign material has been found to be mediated by the Mac-1 receptor molecule. The receptor molecule has also been implicated as having a role in chemokinesis, and chemotaxis of monocytes.

Agents which interfere with the capacity of the Mac-1 receptor molecule to bind to its natural binding ligand are thus capable of impairing all of the above-described Mac-1-dependent functions. Hence, these agents may serve as anti-inflammatory agents in accordance with the present invention. Such agents include ICAM-1, functional derivatives of ICAM-1, Mac-1, functional derivatives of Mac-1, and antibody capable of binding to ICAM-1. All of such agents may be used in accordance with the present invention. The anti-inflammatory agents of the present invention are capable of treating inflammation caused by a reaction of the non-specific defense system.

As used herein, an "antagonist of cellular adhesion" is meant to refer to any molecule capable of inhibiting the process of cell-cell or cell-substrate adhesion. It is possible to determine whether a particular compound is an antagonist by performing an assay of monocyte adhesion to endothelial cells. Suitable assays of cellular adhesion are disclosed, for example, (Keizer, G. D., et al. *Eur. J. Immunol.* 17:1317–1322 (1987)) which reference is herein incorporated by reference. Antagonists of cellular adhesion may be employed as anti-inflammatory agents in the treatment of inflammation. The term "inflammation," as used herein, is meant to include reactions of the specific and non-specific defense systems.

A "reaction of the non-specific defense system" is a response mediated by leukocyte cells incapable of immunological memory. Such cells include neutrophils and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; and cytokine-induced toxicity.

In contrast, a "reaction of the specific defense system" is a reaction mediated by leukocytes having immunological memory. Inflammation is said to result from a reaction of the specific defense system if the inflammation is caused by, mediated by, or associated with a reaction of the specific defense system. Examples of inflammation resulting from a reaction of the specific defense system include the response to antigens such as rubella virus, autoimmune diseases, delayed type hypersensitivity response mediated by T-cells (as seen, for example in individuals who test "positive" in the Mantaux test), etc.

In a preferred embodiment, the anti-inflammatory will comprise ICAM-1 or Mac-1 or, most preferably, a soluble portion thereof.

II. Cellular Adhesion

A. The CD11/CD18 family

The CD11/CD18 family is related structurally and genetically to the larger integrin family of surface receptors that moderate embryogenesis, adhesion to extracellular substrates, and cell differentiation (Hynes, R. O., *Cell* 48:549–554 (1987); Kishimoto, T. K., et al., *Adv. Immunol.* 46:149–182 (1989); Kishimoto, T. K., et al., *Cell* 48:681–690 (1987); Ruoslahti, E., et al., *Science* 238:491–497 (1987)).

The molecules of this family, and their cellular ligands, have been found to mediate cell-cell interactions in inflammation. These proteins have been found to be critical for adhesive functions in the immune system (Kishimoto, T. K., et al., *Adv. Immunol.* 46:149–182 (1989)): monoclonal antibody to LFA-1 block leukocyte adhesion to endothelial cells (Dustin, M. L., et al., *J. Cell. Biol.* 107:321–331 (1988); Smith, C. W., et al., *J. Clin. Invest.* 83:2008–2017 (1989)) and inhibit conjugate formation that is required for antigen-specific CTL killing (Kishimoto, T. K., et al., *Adv. Immunol.* 46:149-182 (1989)), T cell proliferation (Davignon, D., et al., *J. Immunol.* 127:590-595 (1981)), and NK cell killing (Krensky, A. M., et al., *J. Immunol.* 131:611-616 (1983)); monoclonal antibody to Mac-1 block binding of iC3b coated particles (Beller, D. I., et al., *J. Exp. Med.* 156:1000-1009 (1982)), myeloid cell adhesion to endothelial cells (Lo, S. K., et al., *J. Immunol.* 143(10):3325-3329 (1989); Smith, C. W., et al., *J. Clin. Invest.* 83:2008-2017 (1989)), neutrophil homotypic aggregation and chemotaxis (Anderson, D. C., et al., *J. Immunol.* 137:15-27 (1986)); monoclonal antibody to p150,95 block monocyte adhesion to endothelial cells (Anderson, D. C., et al., *J. Immunol.* 137:15-27 (1986); Keizer, G. D., et al., *Eur. J. Immunol.* 17:1317-1322 (1987)) and CTL conjugate formation with target cells (Keizer, G. D., et al., *J. Immunol.* 138:3130-3136 (1987)).

LFA-1 has been found to mediate leukocyte adhesion to unstimulated or stimulated endothelial cells (Dustin, M. L., et al., *J. Cell. Biol.* 107:321-331 (1988); Smith, C. W., et al., *J. Clin. Invest.* 83:2008-2017 (1989)) while Mac-1 has been found to mediate neutrophil and monocyte adhesion to the inflamed endothelium (Luscinskas, F. W., et al., *J. Immunol.* 142(7):2257-2263 (1989)).

B. ICAM-1

ICAM-1 (CD54) is a cell surface adhesion receptor that is a member of the immunoglobulin protein superfamily (Rothlein, R. M., et al., *J. Immunol.* 137:1270-1274 (1986); Staunton, D. E., et al., *Cell* 52:925-933 (1988)), is expressed on a variety of hematopoietic and non-hematopoietic cells, and is upregulated by a variety of inflammatory mediators (Dustin et al., *J. Immunol.*, 137:256-254 (1986)). ICAM-1 is a 90,000-110,000 $M_r$ glycoprotein with a low RNA message level and moderate surface expression on unstimulated endothelial cells; LPS, IL-1, and TNF strongly upregulate ICAM-1 mRNA and surface expression with peak expression at approximately 18-24 hours (Dustin, M. L. et al., *J. Cell. Biol.* 107:321-331 (1988); Staunton, D. E. et al., *Cell* 52:925-933 (1988)). ICAM-1 has five extracellular domains (designated Domains 1, 2, 3, 4, and 5 or D1, D2, D3, D4 and D5) and an intracellular or cytoplasmic domain. The structures and sequence of the domains is disclosed by Staunton, D. E. et al. (*Cell* 52:925-933 (1988), herein incorporated by reference).

ICAM-1 was defined originally as a counter-receptor for LFA-1 (Springer et al., *Ann. Rev. Immunol,* 5:223-252 (1987); Marlin, S. D., *Cell* 51:813-819 (1987); Simmons, D., et al., *Nature* 331:624-627 (1988); Staunton, D. E., *Nature* 339:61-64 (1989); Staunton, D. E., et al., *Cell* 52:925-933 (1988)). The LFA-1-ICAM-1 interaction is partially responsible for lymphocyte adhesion (Dustin, M. L., et al., *J. Cell. Biol.* 107:321-331 (1988); Mentzer, S. J., et al., *J. Cell. Physiol.* 126:285-290 (1986)), monocyte adhesion (Amaout, M. A., et al., *J. Cell. Physiol.* 137:305 (1988); Mentzer, S. J., et al., *J. Cell. Physiol.* 130:410-415 (1987); te Velde, A. A., et al., *Immunology* 61:261-267 (1987)), and neutrophil adhesion (Lo, S. K., et al., *J. Immunol.* 143(10):3325-3329 (1989); Smith, C. W., et al., *J. Clin. Invest.* 83:2008-2017 (1989)) to endothelial cells.

C. The Processes of Cellular Adhesion

Although monoclonal antibody blocking studies had demonstrated convincingly a role for Mac-1 in neutrophil adhesion to both unstimulated and cytokine stimulated endothelial cells (Lo, S. K., et al., *J. Exp. Med.* 169:1779-1793 (1989); Lo, S. K., et al., *J. Immunol.* 143(10):3325-3329 (1989); Luscinskas, F. W., et al., *J. Immunol.* 142(7):2257-2263 (1989); Smith, C. W., et al., *J. Clin. Invest.* 83:2008-2017 (1989)) the identification of the counter-receptor(s) on the endothelial cell surface remained less certain. ICAM-1 and ICAM-2, comprised two candidate ligands for the Mac-1 adhesion molecule.

Through the results of the present invention, it has been now possible to demonstrate that ICAM-1 or Mac-1 transfected COS cells bind to purified Mac-1 or ICAM-1 substrates and that a monoclonal antibody to ICAM-1 inhibits neutrophil adhesion to endothelial cells (Smith, C. W., et al., *J. Clin. Invest.* 83:2008-2017 (1989)) or ICAM-1 containing planar membranes (Smith, C. W., et al., *J. Clin. Invest.* 83:2008-2017 (1989)). Thus, in accordance with the present invention, LFA-1 dependent adhesion to endothelial cells occurs through ICAM-1 (Dustin et al., *J. Cell Biol.,* 107:321-331 (1988); Smith, C. W., et al., *J. Clin. Invest.* 83:2008-2017 (1989)) and ICAM-2. Moreover, the present invention reveals that ICAM-1 is a counter-receptor for Mac-1.

III. Production of ICAM-1, Mac-1 and Their Functional Derivatives

The nucleic acid and protein sequences of the alpha- and beta-subunit of the Mac-1 receptor molecule are disclosed by Kishimoto et al., *Cell* 48:681-690 (1987), and Corbi et al., *Embo J* 6:4023-4029 (1987). The nucleic acid and protein sequences of ICAM-1 are disclosed by Staunton, D. E. et al., *Cell* 52:925-933 (1988), (see FIG. 10). These disclosures permit the use of recombinant DNA technology to produce ICAM-1, Mac-1 and their functional derivatives.

The anti-inflammatory and antiviral agents of the present invention may be obtained by natural processes (such as, for example, by inducing an animal, plant, fungi, bacteria, etc., to produce a non-immunoglobulin antagonist of ICAM-1, or by inducing an animal to produce polyclonal antibodies capable of binding to ICAM-1); by synthetic methods (such as, for example, by using the Merrifield method for synthesizing polypeptides to synthesize ICAM-1, Mac-1 or functional derivatives of either, or protein antagonists of ICAM-1, or Mac-1 (either immunoglobulin or non-immunoglobulin)); by hybridoma technology (such as, for example, to produce monoclonal antibodies capable of binding to ICAM-1); or by recombinant technology (such as, for example, to produce the anti-inflammatory agents of the present invention in diverse hosts (i.e., yeast, bacteria, fungi, cultured mammalian cells, etc.), or from recombinant plasmids or viral vectors) (Kishimoto, T. K., et al., *Cell* 48:681-690 (1987), herein incorporated by reference). The choice of which method to employ will depend upon factors such as convenience, desired yield, etc. It is not necessary to employ only one of the above-described methods, processes, or technologies to produce a particular anti-inflammatory agent; the above-described processes, methods, and technologies may be combined in order to obtain a particular anti-inflammatory agent.

As used herein, a "functional derivative" of ICAM-1 is a compound which is capable of binding to the Mac-1 heterodimer, or to fragments of the Mac-1 heterodimer, and which additionally possesses a biological activity (either functional or structural) that is substantially similar to a biological activity of ICAM-1.

Examples of biological activities include the ability to bind to a member of the LFA family of glycoproteins, the ability to competitively inhibit the binding of anti-ICAM-1 antibody to ICAM-1, or the ability to competitively inhibit the binding of an LFA-1, Mac-1 or p150,95 molecule to ICAM-1, etc.

A "functional derivative" of Mac-1 is a compound which is derivable from the Mac-1 heterodimer, the Mac-1 alpha subunit, or a fragment of the Mac-1 heterodimer, and which additionally can bind to ICAM-1, or a fragment thereof.

The term "functional derivatives" is intended to include the "fragments," "variants," "analogs," or "chemical derivatives" of a molecule. A "fragment" of a molecule such as ICAM-1, or Mac-1 is meant to refer to any polypeptide subset of the molecule. Fragments of ICAM-1 which have ICAM-1 activity and which are soluble (i.e not membrane bound) are especially preferred. Similarly, soluble fragments of Mac-1 which are able to bind ICAM-1 are preferred.

A "variant" of a molecule such as ICAM-1 or Mac-1 is meant to refer to a molecule substantially similar in structure and function to either the entire molecule, or to a fragment thereof. An "analog" of a molecule such as ICAM-1 or Mac-1 is meant to refer to a molecule substantially similar in function to either the entire molecule or to a fragment thereof.

A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in Remington's Pharmaceutical Sciences (1980). "Toxin-derivatized" molecules constitute a special class of "chemical derivatives." A "toxin-derivatized" molecule is a molecule (such as ICAM-1 or one of its functional derivatives) which contains a toxin moiety. The binding of such a molecule to a cell brings the toxin moiety into close proximity with the cell and thereby promotes cell death. Any suitable toxin moiety may be employed; however, it is preferable to employ toxins such as, for example, the ricin toxin, the diphtheria toxin, radioisotopic toxins, membrane-channel-forming toxins, etc. Procedures for coupling such moieties to a molecule are well known in the art.

A "peptidomimetic" of ICAM-1 is a functional derivative of ICAM-1 whose tertiary structure is substantially similar to the tertiary structure of ICAM-1. similarly, a "peptidomimetic" of Mac-1 is a functional derivative of Mac-1 whose tertiary structure is substantially similar to the tertiary structure of Mac-1.

The scope of the present invention is further intended to include those functional derivatives of ICAM-1 and Mac-1 which lack certain amino acid residues, or which contain altered amino acid residues, so long as such derivatives exhibit the capacity to enhance or inhibit cellular adhesion. Such functional derivatives can be produced through chemical or recombinant means.

Functional derivatives having up to about 100 residues may be conveniently prepared by in vitro synthesis. If desired, such fragments may be modified by reacting targeted amino acid residues of the purified or crude protein with an organic derivatizing agent that is capable of reacting with selected side chains or terminal residues. The resulting covalent derivatives may be used to identify residues important for biological activity. Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R'—N—C—N—R') such as 1-cyclohexyl-3-(2-morpholinyl-(4- ethyl ) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking an ICAM-1 or Mac-1 functional derivative molecule to a water-insoluble support matrix or surface for use in the method for cleaving an ICAM-1 or Mac-1 functional derivatives fusion polypeptide to release and recover the cleaved polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or theonyl residues, methylation of the α-amino groups of lysine, arginine, and histidine side chains (T. E. Creighton, *Proteins: Structure and Molecule Properties*, W. H. Freeman & Co., San Francisco, pp. 79-86 (1983)), acetylation of the N-terminal amine, and, in some instances, amidation of the C-terminal carboxyl groups.

Functional derivatives of ICAM-1 or Mac-1 having altered amino acid sequences can also be prepared by mutations in the DNA encoding ICAM-1 or Mac-1. Chemical or radiation mutagens may be employed for this purpose. Chemical mutagens include base analogs (such as, for example, 5-bromouracil, or 2-aminopurine); deaminating agents (such as, for example, nitrous acid, hydroxylamine, etc.); alkylating agents (such as, for example, methyl methanesulphonate, nitrosoguanidine, etc.); or intercolating agents (such as, for example, acridine orange, ethidium bromide, psoralen, etc.). Radiation-induced mutation can be caused by agents such as ultraviolet light, gamma, X ray, etc. Techniques for mutagenizing nucleic acid molecules may be found in Miller, J. H. (In: *Experiments in Molecular Biology*, Cold Spring Harbor Laboratory, Cold Spring Harbor, NY (1972)), and Silhavy, T. J., et al. (In: *Experiments with Gene Fusions*, Cold Spring Harbor Laboratory, Cold Spring Harbor, NY (1984)).

Such agents may be used to randomly mutagenize ICAM-1 or Mac-1 encoding DNA. The mutated gene is then permitted to express an ICAM-1 or Mac-1 protein, and the protein is assayed for its ability to bind to Mac-1 (or ICAM-1). ICAM-1 derivatives that are capable of binding to Mac-1 comprise one class of "functional derivatives." Mac-1 derivatives that are capable of binding to ICAM-1 comprise a second class of "functional derivatives."

Alternatively, and more preferably, site-specific mutagenesis may be employed to produce specific mutations at desired sites of the nucleic acid encoding the ICAM-1 or Mac-1 molecule, thereby producing DNA encoding the functional derivative, and thereafter expressing the DNA in recombinant cell culture. The functional derivatives typically exhibit the same qualitative biological activity as the naturally occurring analog. They may, however, differ substantially in such characteristics with respect to the normally produced ICAM-1 or Mac-1 molecule.

While the site for introducing an amino acid sequence variation is predetermined, the mutation per se need not be predetermined. For example, to optimize the performance of a mutation at a given site, random mutagenesis may be conducted at the target codon or region and the expressed ICAM-1 or Mac-1 functional derivatives screened for the optimal combination of desired activity. Techniques for making substitution mutations at predetermined sites in DNA having a known sequence are well known, for example, site-specific mutagenesis.

Preparation of an ICAM-1 or a Mac-1 functional derivative molecule in accordance herewith is preferably achieved by site-specific mutagenesis of DNA that encodes an earlier prepared functional derivatives or a nonvariant version of the protein. Site-specific mutagenesis allows the production of functional derivatives through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed.

In brief, procedures for site-specific mutagenesis generally entail the synthesis of a synthetic oligonucleotide having a desired and defined DNA sequence. Typically, a primer of about 20 to 25 nucleotides in length is preferred, with about 5 to 10 residues on both sides of the junction of the sequence being altered. Methods for synthesizing such oligonucleotides are disclosed by Itakura, K., et al. (*Ann. Rev. Biochem.* 53:323-356 (1984)), by Adelman et al. (*DNA* 2:183 (1983)), and by Crea et al. (*Proc. Natl. Acad. Sci. (USA)* 75:5765 (1978)), the disclosures of which are incorporated herein by reference.

A nucleic acid molecule which encodes ICAM-1, Mac-1, or a functional derivative of either, is generally subcloned onto a double-stranded vector such as M13, $\phi$X174, etc., whose single strands may be separated one from another (Messing et al., *Third Cleveland Symposium on Macromolecules and Recombinant DNA*, Editor A. Walton, Elsevier, Amsterdam (1981), the disclosure of which is incorporated herein by reference). These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

A single strand of the vector is then incubated in the presence of the synthetic oligonucleotide. Since the DNA of the oligonucleotide is controllably defined, it is possible to construct an oligonucleotide capable of base pairing with any region of the ICAM-1- or Mac-1-encoding nucleic acid. Once base pairing has occurred between the oligonucleotide and the single-stranded plasmid, it is possible to extend the oligonucleotide using DNA polymerase to create a double-stranded DNA molecule which may then be sealed by DNA ligase. When this double-stranded DNA molecule is introduced into a cell (preferably a JM101 cell), semi-conservative DNA replication will result in the production of progeny molecules in which the DNA sequence of the oligonucleotide fragment has been incorporated into the ICAM-1- or Mac-1-encoding sequences.

Thus, after formation, the heteroduplex vector is then used to transform appropriate cells, such as JM101 cells, and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Thus, if one desired to introduce a point mutation, and exogenous DNA sequence into a specific site in the ICAM-1- or Mac-1-encoding sequence, or to create a deletion of nucleotides normally present in such a sequence, one would design an oligonucleotide fragment which contained (or lacked) the mutation or sequence, and then pursue the above-described procedure. In order to introduce such a mutation or exogenous DNA sequence into a particular region of the Mac-1 subunit-encoding nucleic acid, it is necessary to surround the mutation or the exogenous DNA sequence with flanking DNA sequences that are complementary to the DNA sequence of the region whose mutagenesis is desired (Jenkins, F., et al., *Bioessays* 5:244–247 (1986); Doerfler, W., *Angew. Chem. Int. Ed. Engl.* 23:919–931 (1984); Kaina, B., *Biol. Zentralbl.* 99:513–531 (1980); Kunkel, *Proc. Natl. Acad. Sci. (USA)* 82:488–492 (1985); Nisbet, I. T., et al., *Gene Anal. Tech.* 2:23–29 (1985); Hines, J. C., et al., *Gene* 11:207–218 (1980); Messing, J., et al., *Nucl. Acid. Res.* 9:309 (1981)).

Mutations can also be produced through other applications of recombinant DNA technology. For example, the nucleotide sequence of a nucleic acid molecule which encodes ICAM-1 or Mac-1 can be scanned to identify oligonucleotide sites which are recognizable by restriction endonucleases. Such endonucleases can then be used to specifically cleave the nucleic acid sequence at a recognized site. By using a restriction endonuclease that recognizes (and cleaves at) two positions in the ICAM-1- or Mac-1-encoding sequence, it is possible to excise a fragment of this sequence. Alternatively, it is possible to use two different endonucleases for this purpose. By incubating the cleaved molecules in the presence of DNA ligase, it is possible to reseal the ICAM-1- or Mac-1-encoding sequences to form a single sequence (which lacks the excised fragment). If no appropriate restriction endonuclease recognition sites exist in the ICAM-1- or Mac-1-encoding sequences, then such sites may be introduced into the sequences by the site-specific mutagenesis procedure described above.

Mutations may alternatively be introduced by cleaving the ICAM-1- or Mac-1-encoding sequence and "nibbling" the free termini with an exonuclease. By such treatment it is possible to introduce not only deletions, but frame-shift and other types of mutations. This technique is, moreover, capable of introducing novel restriction endonuclease sites into the coding sequence. Methods for using restriction endonucleases, DNA ligases, and exonucleases are disclosed, for example, by Maniatis, T., et al. (In: *Molecular Cloning, A Laboratory Manual*, Cold Spring Harbor Laboratory, Cold Spring Harbor, NY (1982)).

Recombinant DNA techniques may also be used to produce fusion proteins composed of the ICAM-1 or Mac-1 protein (or a functional derivative thereof) and a novel polypeptide. This novel polypeptide is not limited to any particular polypeptide and may comprise either a single amino acid or any set or permutation of amino acids. Such fusion molecules may be produced by ligating a DNA sequence which encodes the novel polypeptide to a DNA sequence which encodes ICAM-1, Mac-1 (or a functional derivative thereof), in a manner which does not introduce a frame-shift mutation. Examples of preferred polypeptides which may be fused to an ICAM-1 gene or a gene of a Mac-1 subunit (or a functional derivative thereof) include eukaryotic or prokaryotic signal sequences (Gilbert, W., et al., U.S. Pat. No. 4,411,994; Casadaban, M., et al., *Proc. Natl. Acad. Sci. (USA)* 76:4530–4533 (1979)), or polypeptides which extend (or diminish) the stability, biological half-life, or potency of ICAM-1 or Mac-1 (or a functional derivative thereof). A fusion protein of an ICAM-1 or Mac-1 molecule or an ICAM-1 functional derivative with an immunoglobin (or fragment thereof) is especially preferred. An excellent review of the methodology of gene fusions is provided by Silhavy, T. J., et al. (In: *Experiments with Gene Fusions*, Cold Spring Harbor Laboratory, Cold Spring Harbor, NY (1984)).

Using the above-described methods, variants of ICAM-1 or Mac-1 can be made. Such variants include, for example, deletions from, or insertions or substitutions of, residues within the amino acid sequence of ICAM-1 or Mac-1. Amino acid sequence deletions generally range from about 1 to 30 residues, more preferably 1 to 10 residues, and typically are contiguous. Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete ICAM-1 or Mac-1 molecule sequence) may range generally from about 1 to 10 residues, more preferably 1 to 5. An example of a terminal insertion includes a fusion of a signal sequence, whether heterologous or homologous to the host cell, to the N-terminus of the molecule to facilitate the secretion of the functional derivative from recombinant hosts. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP Patent Application Publication No. 75,444).

Using the above-described methods, it is possible to produce functional derivatives in which at least one amino acid residue in the ICAM-1 or Mac-1 molecule, and preferably, only one, has been removed and a different residue inserted in its place. Such substitutions preferably are made in accordance with Table 1 when it is desired to modulate finely the characteristics of the ICAM-1 or Mac-1 molecule.

TABLE 1

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |

TABLE 1-continued

| Original Residue | Exemplary Substitutions |
| --- | --- |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the ICAM-1 or Mac-1 molecule. However, when it is difficult to predict the exact effect of the substitution, deletion, or insertion in advance of doing so, one skilled in the art will appreciate that the effect will be evaluated by routine screening assays. For example, a functional derivative typically is made by site-specific mutagenesis of the native ICAM-1 or Mac-1 molecule-encoding nucleic acid, expression of the variant nucleic acid in recombinant cell culture, and, optionally, purification from the cell culture, for example, by immunoaffinity adsorption on an anti-ICAM-1 molecule antibody column (to absorb the functional derivative by binding it to at least one remaining immune epitope).

The activity of the cell lysate or purified ICAM-1 molecule functional derivative is then screened in a suitable screening assay for the desired characteristic. For example, a change in the immunological character of the functional derivative, such as affinity for a given antibody, is measured by a competitive type immunoassay. Changes in immunomodulation activity are measured by the appropriate assay. Modifications of such protein properties as redox or thermal stability, biological half-life, hydrophobicity, susceptibility to proteolytic degradation or the tendency to aggregate with carriers or into multimers are assayed by methods well known to the ordinarily skilled artisan.

IV. Production of Antibodies Capable of Affecting the Binding of ICAM-1 to Mac-1

Antibodies (especially monoclonal antibodies) may be elicited in response to immunization with fragments of the ICAM-1 molecules of the present invention. Such antibodies can be assayed to identify those antibodies which are capable of specifically impairing the ability of ICAM-1 to bind to Mac-1. These antibodies may be used to prevent or attenuate such binding, and thus may be used in the treatment of inflammatory reactions of the non-specific defense system. In addition, such antibodies may be used to prevent or attenuate the binding of viruses (especially rhinoviruses of the major serotype) to ICAM-1.

Although any method of obtaining such monoclonal antibodies may be employed, it is preferable to obtain ICAM-1-binding monoclonal antibodies by immunizing BALB/C mice using the routes and schedules described by Rothlein, R. et al. (J. Immunol. 137:1270–1274 (1986)) with Epstein-Barr virus-transformed peripheral blood mononuclear cells from an LFA-1-deficient individuals. Such cells are disclosed by Springer, T. A., et al,. (J. Exper. Med. 160:1901–1918 (1984)).

Figure 6:
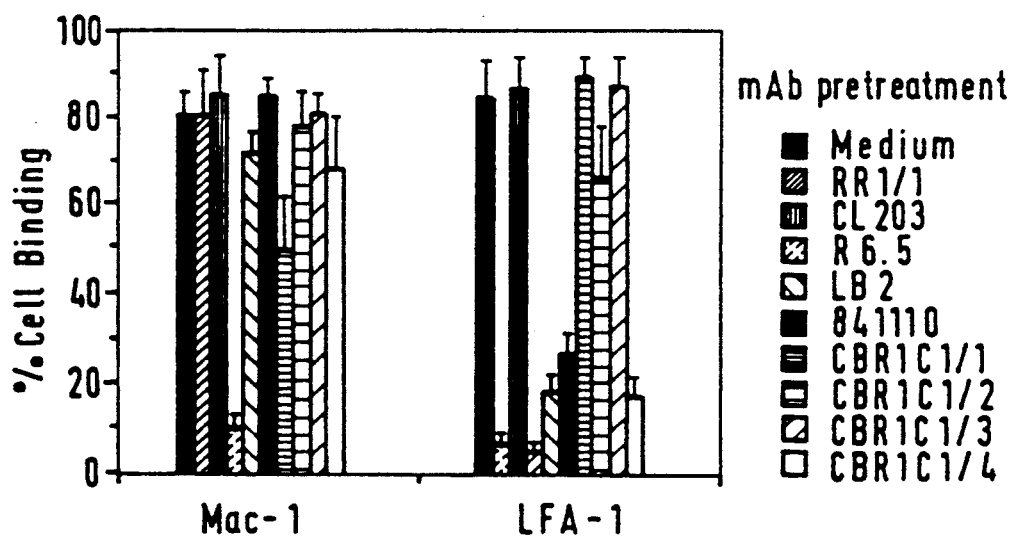
FIG. 6 shows monoclonal antibody inhibition studies of ICAM-1+ L cell adhesion to purified Mac-1 and LFA-1.

In a preferred method for generation and detection of antibodies capable of binding to ICAM-1, mice are immunized with immunoaffinity purified ICAM-1. The spleen cells from the animals are removed, fused with non-secreting myeloma cells and permitted to develop into antibody-producing hybridoma cells. Antibodies are then tested for inhibition of ICAM-1+ L cell adhesion to purified Mac-1 and LFA-1 as shown in FIG. 6. This identifies monoclonal antibodies that differentially inhibit LFA-1 and Mac-1 binding to ICAM-1.

V. Anti-Inflammatory Uses of the Molecules of the Invention

A. ICAM-1 and Mac-1, and Their Functional Derivatives

ICAM-1 is a binding partner of both LFA-1 and Mac-1. As such, ICAM-1 or its functional derivatives may be employed interchangeably with antibodies capable of binding to Mac-1 or to LFA-1 in the treatment of disease. Thus, in solubilized form, such molecules may be employed to inhibit inflammation caused by the interaction of cells expressing Mac-1 with cells expressing ICAM-1. Similarly, Mac-1 or its functional derivatives (preferably solubilized forms of Mac-1) may be employed interchangeably with antibodies capable of binding to ICAM-1 to inhibit inflammation caused by the interaction of cells expressing ICAM-1 with cells expressing Mac-1. Such inflammation is generally mediated by a reaction of the non-specific defense system. Similarly, such derivatives can also be used to inhibit inflammation caused by the interaction of cells expressing ICAM-1 with cells expressing LFA-1. Such inflammation is generally mediated by a reaction of the specific defense system.

The present invention discloses that the sites of interaction between ICAM-1 and LFA-1 are severable from those sites of ICAM-1 which interact with Mac-1. Thus, one may produce novel functional derivatives of ICAM-1 which are substantially capable of binding to either LFA-1 or Mac-1 but are substantially incapable of binding to Mac-1 or LFA-1. Also, one can produce derivatives of ICAM-1 which are substantially incapable of binding LFA-1 and Mac-1, but are substantially able to bind human rhinovirus. Among the preferred functional derivatives of the present invention are functional derivatives (especially soluble derivatives) of ICAM-1 which contain Domains 1, 2, 3, 4 and 5 of ICAM-1 D1, residues 1–88, D2, residues 89–185, D3, residues 185-284, D4, residues 285-385, and D5, residues 386-453, as described in Staunton et al., *Cell* 52:925-933 (1988).

Thus, an especially preferred soluble derivative of ICAM-1 is a molecule which is substantially capable of binding to the LFA-1 of an LFA-1-expressing cell, but which is substantially incapable of binding to Mac-1. Examples of such molecules include ICAM-1 molecules which possess Domain 1, Domains 1 and 2, Domains 1, 2, and 4, but which lack Domain 3. Additional examples include ICAM-1 derivatives which comprise Domain 3, but which contain a mutation in Domain 3 that renders the molecule substantially incapable of binding Mac-1. Particularly preferred mutations in Domain 3 are mutations in ICAM-1 residue 229-231, or 254-256 of ICAM-1. Such mutations render ICAM-1 substantially incapable of binding Mac-1. Such derivatives are desirable in situations in which one wishes to treat inflammatory reactions of the specific defense system without affecting the inflammatory reactions of the non-specific defense system.

In a like manner, the present invention permits one to produce novel functional derivatives of ICAM-1 which are substantially capable of binding to the Mac-1 of a Mac-1-expressing cell, but which are substantially incapable of binding to LFA-1. Examples of such molecules include ICAM-1 molecules which lack Domain 1, of ICAM-1, and those which contain Domains 1, 2, 3, 4 and 5 of ICAM-1, but contain a mutation in Domains 1 or 2 of ICAM-1. Particularly preferred mutations are those in ICAM-1 residue(s) E34, Q58ED, or Q73 of Domain 1 of ICAM-1. Among preferred ICAM-1 functional derivatives which lack Domain 1 are those comprising Domains 3 and 4 of ICAM-1. Such derivatives are desirable in situations in which one wishes to treat inflammatory reactions of the non-specific defense system without affecting the inflammatory reactions of the specific defense system.

A second way in which one can obtain an ICAM-1 derivative which can be used to treat inflammatory reactions of the non-specific defense system without affecting the inflammatory reactions of the specific defense system is by increasing the relative ability of the derivative to bind to Mac-1 rather than LFA-1. One means of realizing this goal is by producing an ICAM-1 functional derivative that lacks one or more glycosylation site(s). Such a derivative is capable of enhanced binding ability to Mac-1. Most preferred for this purpose is the loss of a glycosylation site at ICAM-1 residue N269, N240 or N358 of ICAM-1.

As used herein, a functional derivative of a molecule is said to be "substantially capable" of binding to another molecule if its ability to bind that molecule is approximately the same as the ability of a natural precursor of that derivative to bind the same molecule. Thus, for example, a functional derivative of ICAM-1 is said to be "substantially capable" of binding to Mac-1 (or to LFA-1) if the derivative has approximately the same ability to bind Mac-1 (or LFA-1) as ICAM-1 itself.

As used herein, a functional derivative of a molecule is said to be "substantially incapable" of binding to another molecule if its ability to bind that molecule is substantially different (for example less than 50%) from the ability of a natural precursor of that derivative to bind the same molecule. Thus, for example, a functional derivative of ICAM-1 is said to be "substantially incapable" of binding to Mac-1 (or to LFA-1) if the derivative has less than 50% of the ability to bind Mac-1 (or LFA-1) that ICAM-1 itself has.

The solubilized derivatives referred to above are derivatives which are not bound to a membrane of a cell. Such derivatives may comprise truncated molecules which lack a transmembrane domain. Alternatively, they may comprise mutant forms of the natural molecules which lack the capacity to be bound (or stably bound) to the membrane of a cell even though they contain a transmembrane domain. The domain structure of ICAM-1, soluble derivatives of ICAM-1 and their preparation are disclosed by Marlin, S. D. et al., *Nature* 344:70-72 (1990). As described by Marlin, et. al., soluble derivatives can be generated by introducing a stop codon in the sequence encoding ICAM-1 after domain 5 such that the ICAM-1 coding sequence will lack the transmembrane domain.

Yet another type of preferred molecule is a soluble derivative of Mac-1 which is substantially capable of binding to the ICAM-1 of an ICAM-1-expressing cell, but which is substantially incapable of preventing the binding to another member of the LFA-1 family of molecules to ICAM-1. Examples of such molecules include Mac-1 molecules which do not impair the ability of LFA-1 to bind to Domain 1 of ICAM-1. Such molecules are desirable since they can affect inflammatory reactions of the non-specific defense system without affecting the reactions of the specific defense system. Such Mac-1 functional derivatives can be identified, for example, by screening a potential Mac-1 functional derivative for its inability to impair the ability of ICAM-1 to bind to LFA-1.

ICAM-1, or its functional derivatives may be used in the same manner as anti-Mac-1 antibodies to decrease the immunogenicity of therapeutic or diagnostic agents. Similarly, Mac-1, or its functional derivatives may be used in the same manner as anti-ICAM-1 antibodies to decrease the immunogenicity of therapeutic or diagnostic agents.

ICAM-1, or Mac-1, or the functional derivatives of either, may be used to block the metastasis or proliferation of tumor cells which express either Mac-1 or ICAM-1 on their surfaces. A variety of methods may be used to accomplish such a goal. For example, the migration of certain cells requires LFA-1-ICAM-1 binding. Toxin-derivatized molecules, capable of binding either ICAM-1 or Mac-1 may be administered to a patient. When such toxin-derivatized molecules bind to tumor cells that express ICAM-1 or Mac-1α member of the LFA-1 family of molecules, the presence of the toxin kills the tumor cell thereby inhibiting the proliferation of the tumor.

B. Antibody Capable of Binding ICAM-1

Monoclonal and polyclonal antibodies capable of binding to ICAM-1 and thereby preventing the binding of ICAM-1 to Mac-1 are highly suitable as anti-inflammatory agents in a mammalian subject. Monoclonal antibodies are especially preferred for such use. Significantly, such agents differ from general anti-inflammatory agents in that they are capable of selectively inhibiting adhesion, and do not offer other side effects such as nephrotoxicity which are found with conventional agents. Such monoclonal antibodies can be used to treat inflammation resulting from a reaction of the non-specific defense system.

Since LAD patients that lack LFA-1 do not mount an inflammatory response, it is believed that antagonism of LFA-1's natural ligand, ICAM-1, will also inhibit an inflammatory response. The ability of antibodies against ICAM-1 to inhibit inflammation provides the basis for their therapeutic use in the treatment of chronic inflammatory diseases and autoimmune diseases such as lupus erythematosus, autoimmune thyroiditis, experimental allergic encephalomyelitis (EAE), multiple sclerosis, some forms of diabetes Reynaud's syndrome, rheumatoid arthritis, etc. Such antibodies may also be employed as a therapy in the treatment of psoriasis. In general, the monoclonal antibodies capable of binding to ICAM-1 may be employed in the treatment of those diseases currently treatable through steroid therapy.

Of special interest to the present invention are antibodies to ICAM-1 (or their functional derivatives), which are substantially capable of inhibiting or preventing the binding of ICAM-1 to Mac-1, but are substantially incapable of inhibiting or preventing the binding of ICAM-1 to LFA-1. Such antibodies can be used to treat inflammation of the non-specific defense system without affecting the reactions of the specific defense system. An example of such an anti-ICAM-1 antibody is monoclonal antibody CBRIC1/1. A hybridoma cell line which secretes this monoclonal antibody was deposited with the American Type Culture Collection on Nov. 14, 1990, and accorded ATCC accession number HB10597.

Also of special interest to the present invention are antibodies to ICAM-1 (or their functional derivatives), which are substantially capable of inhibiting or preventing the binding of ICAM-1 to LFA-1, but are substantially incapable of inhibiting or preventing the binding of ICAM-1 to Mac-1. Such antibodies can be used to treat inflammation of the specific defense system without affecting the reactions of the non-specific defense system. Examples of such antibodies are anti-ICAM-1 monoclonal antibodies RR1/1 (Rothlein, R. M., et al., *J. Immunol.* 137:1270–1274 (1986)), LB2 (Clark, E. A., et al., *Hum. Immunol.* 16:100–113 (1986)), 84H10 (Makgoba, M. W., et al., *Nature* 331:86–88 (1988)), and CBRIC1/4.

The anti-ICAM-1 antibody R6.5 (Smith, C. W., et al., *J. Clin. Invest.* 82:1746–1756 (1988)) is capable of preventing both Mac-1 and LFA-1 binding to ICAM-1. It is thus a preferred antibody inflammatory reactions involving both the specific and non-specific defense systems.

As indicated above, both polyclonal and monoclonal antibodies may be employed in accordance with the present invention. Antibodies that are produced in humans, or are "humanized" (i.e. non-immunogenic in a human) by recombinant or other technology are especially preferred. Such antibodies are the equivalents of the monoclonal and polyclonal antibodies disclosed herein, but are less immunogenic, and are better tolerated by the patient.

Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl. Cancer Inst.* 80:1553–1559 (1988); all of which references are incorporated herein by reference). General reviews of "humanized" chimeric antibodies are provided by Morrison, S. L. (*Science,* 229:1202–1207 (1985)) and by Oi, V. T. et al., *BioTechniques* 4:214 (1986); which references are incorporated herein by reference).

Suitable "humanized" antibodies can be alternatively produced by CDR or CEA substitution (Jones, P. T. et al., *Nature* 321:552–525 (1986); Verhoeyan et al., *Science* 239:1534 (1988); Beidler C. B. et al., *J. Immunol.* 141:4053–4060 (1988); all of which references are incorporated herein by reference).

VI. Administration of the Molecules of the Present Invention

Since Mac-1 is expressed on cells which are capable of binding to endothelial tissue, the administration of ICAM-1, or a functional derivative of ICAM-1, to a patient provides a means for imaging or visualizing endothelial tissue. Similarly, administration of Mac-1 to a patient permits one to visualize sites of ICAM-1 expression, and thereby permits the detection of sites of inflammation. Moreover, such procedures provide diagnostic information concerning the quantity and distribution of the binding ligands of the Mac-1 receptor molecule or of ICAM-1 which are present on the visualized tissue.

In such a use, the administered molecules of the present invention are detectably labeled, through the use of radioisotopes, affinity labels (such as biotin, avidin, etc.) fluorescent labels, paramagnetic atoms, etc. Procedures for accomplishing such labeling are well known to the art. The antibodies (or fragments thereof) may be detectably labeled through the use of radioisotopes, enzyme labels, fluorescent labels, paramagnetic labels, electron-dense labels, etc. The administration of such labeled molecules into an individual will identify sites of inflammation. Such detectable labels can also be used to assay the status of a patient's immune system. Clinical application of antibodies in diagnostic imaging are reviewed by Grossman, H. B., *Urol. Clin. North Amer.* 13:465–474 (1986)), Unger, E. C. et al., *Invest. Radiol.* 20:693–700 (1985)), and Khaw, B. A. et al., *Science* 209:295–297 (1980)).

The ability of monocytes to migrate spontaneously to sites of inflammation is dependent upon Mac-1 (Keizer, G. D., et al., *Eur. J. Immunol.* 17:1317–1322 (1987)). Such migration may be inhibited by administrating ICAM-1, or functional derivatives of ICAM-1 to a patient.

Similarly, the ability of monocytoid cells to adhere to endothelial cells, and the ability of monocytoid cells to undergo chemotaxis, chemokinesis, or phagocytosis has been found to be dependent upon Mac-1 (Keizer, G. D., et al., *Eur. J. Immunol.* 17:1317–1322 (1987)). Any of the anti-inflammatory agents of the present invention may be employed to inhibit such activities.

The molecules of the present invention are said to be "substantially free of natural contaminants" if preparations which contain them are substantially free of materials with which these products are normally and naturally found.

The present invention extends to antibodies, and biologically active fragments thereof, (whether polyclonal or monoclonal) which are capable of binding to ICAM-1. Such antibodies may be produced either by an animal, or by tissue culture, or recombinant DNA means.

In providing a patient with antibodies, or fragments thereof, capable of binding to ICAM-1, or when providing ICAM-1, Mac-1 (or a fragment, variant, or derivative thereof) to a recipient patient, the dosage of administered agent will vary depending upon such factors as the patient's age, weight, height, sex, general medical condition, previous medical history, etc. In general, it is desirable to provide the recipient with a dosage of antibody which is in the range of from about 1 pg/kg to 10 mg/kg (body weight of patient), although a lower or higher dosage may be administered. When providing ICAM-1 or Mac-1 molecules or their functional derivatives to a patient, it is preferable to administer such molecules in a dosage which also ranges from about 1 pg/kg to 10 mg/kg (body weight of patient) although a lower or higher dosage may also be administered. As discussed below, the therapeutically effective dose can be lowered if the anti-ICAM-1 antibody is additionally administered with an anti-LFA-1 antibody, or its equivalent.

As used herein, one compound is said to be additionally administered with a second compound when the administration of the two compounds is in such proximity of time that both compounds can be detected at the same time in the patient's serum.

The molecules of the present invention may be administered to patients intravenously, intramuscularly, subcutaneously, enterally, or parenterally. When administering such molecules by injection, the administration may be by continuous infusion, or by single or multiple boluses.

The anti-inflammatory agents of the present invention are intended to be provided to recipient subjects in an amount sufficient to suppress inflammation. An amount is said to be sufficient to "suppress" inflammation if the dosage, route of administration, etc. of the agent are sufficient to attenuate or prevent inflammation.

The anti-inflammatory agents of the present invention may be administered either alone or in combination with one or more additional immunosuppressive agents (especially to a recipient of an organ or tissue transplant). The administration of such compound(s) may be for either a "prophylactic" or "therapeutic" purpose. When provided prophylactically, the compound(s) are provided in advance of any inflammatory response or symptom. The prophylactic administration of the compound(s) serves to prevent or attenuate any subsequent inflammatory response. When provided therapeutically, the compound(s) is provided at (or shortly after) the onset of a symptom of actual inflammation. The therapeutic administration of the compound(s) serves to attenuate any actual inflammation. The anti-inflammatory agents of the present invention may, thus, be provided either prior to the onset of inflammation (so as to suppress an anticipated inflammation) or after the initiation of inflammation.

A composition is said to be "pharmacologically acceptable" if its administration can be tolerated by a recipient patient. Such an composition is said to be administered in a "therapeutically effective amount" if the amount administered is physiologically significant. An agent is physiologically significant if its presence results in a detectable change in the physiology of a recipient patient.

The molecules of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton PA (1980)). In order to form a pharmaceutically acceptable composition suitable for effective administration, such compositions will contain an effective amount of anti-ICAM antibody, or ICAM-1 or Mac-1 molecule, or their functional derivatives, together with a suitable amount of carrier vehicle.

Additional pharmaceutical methods may be employed to control the duration of action. Control release preparations may be achieved through the use of polymers to complex or absorb the therapeutic agents of the invention. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate anti-ICAM-1 antibody or ICAM-1 molecules, or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Having now generally described the invention, the same will be more readily understood through reference to the following examples which are provided by way of illustration, and are not intended to be limiting of the present invention, unless specified.

EXAMPLE 1

Methods For Investigating The Interaction Between Mac-1 and ICAM-1

Recent studies by Smith, C. W. et al. (*J. Clin. Invest.* 83:2008–2017 (1989); *J. Clin. Invest.* 82:1746–1756 (1988); herein incorporated by reference) suggested to the inventors that LFA-1 and Mac-1 could cooperate in neutrophil adherence to endothelial cells; unstimulated neutrophils bind primarily through surface LFA-1 while fMLP activated neutrophils attach mostly through Mac-1. Mac-1 and LFA-1 both may be interacting with ICAM-1 as a monoclonal antibody to ICAM-1 thoroughly blocks CD18 dependent, fMLP-stimulated neutrophil adhesion to unstimulated endothelial cells (Smith, C. W. et al., *J. Clin. Invest.* 82:1746–1756 (1988)). Because monoclonal antibodies to LFA-1 and Mac-1 also abrogate neutrophil attachment to planar membranes containing ICAM-1 (Smith, C. W., et al., *J. Clin. Invest.* 83:2008-2017 (1989)), the work of Smith et al. supported the conclusion that neutrophil adhesion to endothelial cells was partially ICAM-1-LFA-1 and ICAM-1-Mac-1 dependent.

In contrast, Lo, S. K., et al. (*J. Immunol.* 143(10):3325-3329 (1989)) disclosed that when phorbol ester stimulated neutrophils adhere to unstimulated endothelial cells, while both Mac-1 and LFA-1 are involved, only LFA-1 interacted with ICAM-1. In addition, they found that when macrophages were plated on ICAM-1 substrates, only LFA-1 was down-modulated from the apical portion of the cell surface. These results supported the conclusion that Mac-1 did not bind ICAM-1, but rather, interacted with an uncharacterized endothelial cell surface receptor.

To resolve this paradox, reciprocal adhesion studies were conducted using immunoaffinity purified Mac-1 and ICAM-1, and transfected cells expressing ICAM-1, Mac-1 and LFA-1.

Monoclonal Antibodies

The following murine monoclonal antibody against human antigens were from ascites: LPM19c (anti-CD11b, IgG2a); Uciechowski, P., et al., In *Leukocyte Typing IV: White Cell Differentiation Antigens*, W. Knapp (ed.), Oxford University Press, Oxford, pp. 543-551 (1989)), W6/32 (anti-HLA A, B, C, IgG2a) (Barnstable, C. J., et al., *Cell* 14:9-20 (1978)), TS1/22 (anti-CD11a, IgG1) (Sanchez-Madrid, F., et al., *Proc. Natl. Acad. Sci. USA* 79:7489-7493 (1982)), YFC51.1 (anti-CD18,rate IgG2b) (Uciechowski, P., et al., In *Leukocyte Typing IV: White Cell Differentiation Antigens*. W. Knapp (ed.), Oxford University Press, Oxford, pp. 543-551 (1989)), CBRIC2/1 and CBRIC2/2 (anti-ICAM-2, IgG2a) and TS2/I6 (anti-CD29, IgGI) (Sanchez-Madrid, F., et al., *Proc. Natl. Acad. Sci. USA* 79:7489-7493 (1982)). The following ICAM-1 monoclonal antibody were used as purified IgG: CL203 (Maio, M., et al., *J. Immunol.* 143:181-188 (1989)), LB-2 (Clark, E. A., et al., *Hum. Immunol.* 16:100-113 (1986)), 84H10 (Makgoba, M. W., et al., *Nature* 331:86-88 (1988)).

RR1/1 Fab$_2$ (IgGI) (Rothlein, R. M. et al., *J. Immunol.* 137:1270-1274 (1986)) were prepared by pepsin digestion after Protein A affinity chromatography (Parham, P., In *Immunological Methods in Biomedical Sciences*, Weir, D. M., et al. (eds.), Blackwell, Oxford (1983)). R6.5 (IgG2a) (Smith, C. W., et al., *J. Clin. Invest.* 82:1746-1756 (1988)) IgG and Fab were obtained from Boehringer Ingelheim Pharmaceuticals, Ridgefield, CT.

Monoclonal antibodies CBRIC1/1, CBRIC1/2, CBRIC1/3, CBRIC1/4 (anti-ICAM-1 monoclonal antibody), M1/42 (anti H-2, rat IgG2a) (Springer, T. A., In *Monoclonal Antibodies*, Kennett, R. H., et al. (eds.), Plenum Press, New York, pp. 185-217 (1980)) and X63 (nonbinding antibody, IgG1) were used as tissue culture supernatants. For inhibition assays ascites fluids were used at 1/400 dilutions, purified IgG were used at 20-25 μg/ml, Fab$_2$ were used at 20 μg/ml, Fab were used at 50 μg/ml, and tissue culture supernatants were used at 1/2. Protein A purified TS1/18 (anti-CD18, IgG1) (Sanchez-Madrid, F., et al., *Proc. Natl. Acad. Sci USA* 79:7489-7493 (1982)) and LM2/1 (anti-CD11b, IgGI) (Miller, L. J., et al., *J. Immunol.* 137:2891-2900 (1986)) were iodinated and used for site density measurements as described by Dustin, M. L., et al. (*Nature* 341:619-624 (1989), herein incorporated by reference); TSI/18 recognizes only the intact α/β heterodimer.

Protein Purification: Mac-1, LFA-1 and ICAM-1

Mac-1 was purified from leukocyte lysates by a modification of the procedure of Dustin, M. L. et al. (*Nature* 341:619-624 (1989)) and Miller, L. J., et al. (*Immunol.* 138:2381-2383 (1987)), both references herein incorporated by reference.

Briefly, to obtain 500 μg of the purified functional heterodimer, 10 g of frozen peripheral blood leukocytes were solubilized in 200 ml of lysis buffer (100 mM Tris HCl pH 8.0, 150 mM NaCl, 2 mM MgCl$_2$, 1% Triton X-100, 5 mM iodoacetamide, 0.025% NaN$_3$, 1 mM phenylmethyl sulfonylfluoride, 1 mM disopropylfluorophosphate, 0.2 TIU/ml Aprotinin) for one hour at 4° C. while stirring gently. The resultant lysate was centrifuged at 10,000×g for two hours at 4° C.; the supernatant was decanted and then ultracentrifuged at 100,000×g (Ti45, Beckman) for one hour.

The clarified lysate was precleared with human IgG coupled to Sepharose CL-4B; 40 μl of a 1:1 slurry of IgG-Sepharose was added per ml of lysate and rotated overnight at 4° C. The Sepharose was pelleted and the precleared lysate was then passed over an LM2/1 (anti-CD11b; IgG1) immunoafinity column (bed volume 6 ml, 3 mg/ml of LM2/1). This was prepared by attaching protein A purified LM2/1 to cyanogen bromide activated Sepharose (March, S. C., et al., *Anal. Biochem.* 60:149-152 (1974)).

The column was prequilibrated with 10 bed volumes of 50 mM Tris-HCl pH 8.0, 150 mM NaCl, 2 mM MgCl$_2$ 0.1% Triton-X-100, and the precleared lysate was loaded at 10 mls per hours. The column wa sequentially washed at 20 mls per hour with 10 bed volumes of 50 mM Tris-HCl pH 8.0, 150 mM NaCl, 2 mM MgCl$_2$, 1% n-octyl β-D-glucopyranoside into tubes with neutralizing buffer (10% by volume 1M Tris-HCl pH 7.4). The peak fractions are pooled, aliquoted, and stored at −80° C. for 3-6 months without loss of activity.

LFA-1 was purified by immunoaffinity chromatography as described by Dustin, M. L. et al. (*Nature* 341:619-624 (1989)) except that peripheral blood leukocyte lysates were substituted.

ICAM-1 was purified by immunoaffinity chromatography as described by Marlin, S. D. et al. (*Cell* 51:813-819 (1987)).

SDS-PAGE

Protein samples were run on 7-10% sodium dodecyl sulfate polyacrylamide (Laemmli, U. K., *Nature* 227:680-685 (1970)) reducing gels containing 5% β-mercaptoethanol and silver stained as described by Morrissey, J. H. (*Anal. Biochem.* 117:307-310 (1981)).

Tissue Culture, Transfection, and Cell Preparation

COS cells were grown on 10 or 15 cm tissue culture treated plates (Falcon) in RPMI 1640 with 10% fetal calf serum, 5 mM glutamine and 50 μg/ml gentamycin. Cells were transfected at approximately 50-60% confluency in 10 cm plates with 4-6 μg of CsCl purified (Maniatis, T., et al., In *Molecular Cloning: A Laboratory Manual*, Cold Spring Harbor Laboratory Press, Cold Spring Harbor, NY (1982), herein incorporated by reference) ICAM-1 DNA (Staunton, D. E., et al., *Cell* 61:243-254 (1990)) or cotransfected with 6 μg Mac-1 or LFA α plus 6 μg β cDNA (Hibbs, M. L., et al., *J. Clin. Invest.* 85:674-681 (1990); Larson, R. S., et al., *Cell Reg.*

1:359-367 (1990)) by the DEAE-Dextran method for four hours at 37° C. (Aruffo, A., et al., *Proc. Natl. Acad. Sci. USA* 84:8573-8577 (1987); Kingston, R. E., In *Current Protocols in Molecular Biology*, Greene Publishing Associates, pp. 9.0.1-9.9.6 (1987)). After 72 hours cells were eluted from the tissue culture plates prior to functional assays with PBS (phosphate buffered saline), 5 mM EDTA at 37° C. for five minutes.

ICAM-1+ L cell stables were generated as described by Chen, C. A. et al. (*BioTechniques* 6(7):632-637 (1988), herein incorporated by reference). Briefly, murine L cells (tk-) were seeded onto 6 cm tissue culture dishes and grown to 10-20% confluency over two days. ICAM-1 cDNA in the plasmid CDM8 (Staunton, D. E., et al., *Cell* 61:243-254 (1990)) (10 μg) and plasmid containing a thymidine kinase selection marker (100 mg) were mixed with 0.2 ml $CaCl_2$ and 0.2 ml of 50 mM N-N-Bis-2-amino-ethanesulfonic acid, 280 mM NaCl, 1.5 mM $Na_2HPO_4$, pH 6.95 and incubated at room temperature for 10-20 minutes. The calcium phosphate-DNA solution (0.4 ml) was added dropwise to the plated cells and incubated at 35° C. in a 3% $CO_2$ incubator. Twenty four hours later, the cells were washed with regular DMEM media and grown at 37° C. in a 5% $CO_2$ incubator until day 3 when HAT (100 μM hypoxanthine, 400 nM aminopterin, 16 μM thymidine) selection was initiated.

Cells with high ICAM-1 expression were identified by flow cytometry after single colony picks with a cloning cylinder. ICAM-1+ L cells were maintained in a selection media that consisted of DMEM with 10% heat inactivated fetal calf serum, 5 mM glutamine, 50 μg/ml gentamycin, and supplemented with HAT. Untransfected L cells were maintained in DMEM without HAT.

Human umbilical vein endothelial cells (HUVEC) were cultured to low passage number (2-5) on tissue culture plates pre-coated with fibronectin (50 μg/ml) in M199 media supplemented with 20% heat-inactivated fetal calf serum, 100 μg/ml heparin, 100 μg/ml gentamycin (Dustin, M. L., et al., *J. Cell. Biol.* 107:321-331 (1988)).

LPS treatment was performed by adding 1 μg/ml of *E. coli* lipopolysaccharide (endotoxin) 24 hours prior to harvesting of cells. Cytokine stimulation was performed by addition of 5 U/ml of rIL-1β (Genentech, CA).

To elute HUVEC for the two color fluorescence studies, cells were treated with PBS, 5 mM EDTA at 37° C. for five to ten minutes.

Neutrophils were isolated from the whole blood of healthy volunteers by dextran sedimentation, Ficoll gradient centrifugation, and hypotonic lysis were performed as described by English, D., et al. (*J. Immunol. Methods* 5:249 (1974)). Prior to experimental manipulation, neutrophils are stored at room temperature in Hank's balanced salt solution, 10 mM HEPES pH 7.3, 0.5% human serum albumin (HHHSA).

Cell Conjugation Experiments

A dual fluoresoence cell conjugate assay was performed by modification of the protocol of Luce, G. G. et al. (*BioTechniques* 3:270-272 (1985), herein incorporated by reference).

Briefly $10^8$ neutrophils were washed twice in HHHSA, resuspended in 10 ml of a filtered (0.2 μm) solution of 40 μg/ml hydroethidine (HE, Polysciences) in HHHSA, and incubated for 35 minutes at 37° C. while gently rocking the sample. HUVEC ($2 \times 10^7$) were eluted from T150 cm flasks with PBS, 5 mM EDTA, washed thrice in RPMI 1640, 20 mM HEPES pH 7.3, 5% heat inactivated fetal calf serum (RPMTHFS), resuspended in 10 ml of a 200 μM solution of sulfofluorescein diacetate (SFDA, Molecular Probes), and incubated also for 30 minutes at 37° C. Subsequently, cells were washed four times in RPMI 1640, 10 mM Hepes pH 7.3, 0.5% HSA, 5% heat-inactivated human serum and resuspended as follows: neutrophils, $1 \times 10^7$ cells/ml; HUVEC, $2 \times 10^6$ cells/ml. The assay was performed in the presence of heat inactivated human serum (5%) to prevent Fc receptor crosslinking with the monoclonal antibodies. The appropriate antibodies were added to both cell types and preincubated for 25 minutes at room temperature.

Neutrophils (150 μl) and HUVEC (250 μl) were added to a 24 well plate (Falcon) and the following experimental protocol was used (all incubations were at 37° C. while shaking at 75 rpm on a gyratory shaker (New Brunswick Scientific, NJ): five minute preincubation, $1 \times 10^{-7}$ M fMLP addition, ten minute incubation. Conjugates were recovered after pipetting the solution thrice (small aggregates may settle) and quantitated as the percentage of HUVEC found in two color conjugates by flow cytometry with either an EPICS V (Coulter, Hialeah, FL) or a FACScan (Becton Dickinson).

Cell Binding to Purified Proteins

Purified Mac-1 or LFA-1 was diluted from ⅛-1/120 depending on protein content (judged by SDS-PAGE and radioimmunoassay (Dustin, M. L., et al., *Nature* 341:619-624 (1989))) in 20 mM Tris pH 7.4, 150 mM NaCl, 2 mM $MgCl_2$ with an octyl glucoside detergent concentration ranging from 0.1% to 0.01% and plated over the entire surface of 35 mm Petri dishes, as a 40 μl demarcated spot on 60 mm Petri dishes, or in 50 μl for each well of 96 well plates (Linbro-Itertek) for 90 minutes at room temperature Staunton, D. E., *Nature* 339:61-64 (1989). Plates and dishes were blocked subsequently by three washes with and subsequent incubation in PBS, 2 mM $MgCl_2$, 0.5% HSA (PBSMH) for two hours at 37° C. For the COS cell adhesion assay to Mac-1, lower site densities of Mac-1 (<500 sites/μm²) were used to avoid a background cell binding that is due to the expression of an endogenous ligand for Mac-1 on the COS cell surface; this site density allowed ICAM-1-expressing COS cells to adhere but did not sustain binding of COS cells that had been transfected with the vector alone.

For the 96 well plate assay, unstimulated, 18 hour IL-1β or 24 hour LPS stimulated HUVEC were eluted from tissue culture plates with PBS, 5 mM EDTA, washed twice in HHHSA, resuspended to $10^6$ cells/ml, labelled with 50 μCi/ml Sanchez-Madrid et al., *J. Exp. Med.* 158:1785-1803 (1983) Cr for one hour at 37° C., washed twice in HHHSA, twice in PBSMH +0.2% glucose, and along with the Mac-1 treated plates were preincubated for 25 minutes at room temperature with appropriate antibodies. HUVEC (50 μl of $10^6$ cells/ml) were added to each well and the binding assay was performed at room temperature for one hour. Unbound cells were removed by a high stringency aspiration wash procedure that used a 26 gauge needle (Dustin, M. L., et al., *Nature* 341:619-624 (1989)). Bound cells were eluted with 0.2M NaOH or PBS, 25 mM EDTA and quantitated by γ emission. The same protocol was used with L cells except that RPMI 1640, 20 mM HEPES pH 7.3, 5% FCS, 0.1% HSA was substituted as the binding buffer, the cells were centrifuged at 300 rpm for five minutes onto Mac-1 substrates, the incubation was performed at 37° C., and only two aspiration washes were performed.

For the 35 and 60 mm Petri dish assays, transfected COS cells or L cells were eluted from tissue culture plates with PBS, 5 mM EDTA or RPMI, 10 mM EDTA. COS cells were washed twice in HHHSA, resuspended in HHHSA to $8 \times 10^5$ cells/ml, and labelled with 50 µCi/ml Cr for one hour (Sanchez-Madrid et al., *J. Exp. Med.* 158:1785-1803 (1983)). Excess label was washed out and the cells were resuspended to $8 \times 10^5$/ml in PBS, 1.5 mM $MgCl_2$, 0.5 mM $CaCl_2$, 0.2% glucose, 0.5% HSA. L cells were washed thrice with PBS, 2 mM $MgCl_2$, 5% FCS, 0.1% HSA. Cells were preincubated with appropriate antibodies for 30 minutes at room temperature, added to Petri dishes, and incubated for 50 minutes at 37° C. Unbound COS or L cells were removed by three successive washes with 1 ml of binding buffer that was added and then swirled gently across the plate. With COS cell experiments, after washing, the plates were inspected visually for bound cells, assessed qualitatively, and the adherent population was eluted with 1 ml PBS, 25 mM EDTA (15 minutes at 37° C.) and quantitated by $\gamma$ emission. For L cell experiments, after washing, bound cells were quantitated by visually scoring the number of cells in 4-5 high power light microscope fields for each experimental point. This number was divided into the input number of cells per field to obtain the percentage of cells binding.

Flow Cytometry $0.5-1.0 \times 10^5$ cells in 50 µl in HHHSA were added to V-bottom microtiter plates containing 50 µl of antibody supernatants or 50 µl of a 1/200 dilution of antibody ascites. The plate was sealed with tape and shaken on a Dynatech plate shaker for 45 minutes at 4° C. Cells were pelleted (2000 rpm, two minutes, 4° C.) and washed thrice (150 µl) with HHHSA, and resuspended in 100 µl of a 1/20 dilution of purified FITC conjugated goat anti-mouse IgG light + heavy chain antisera (Zymed, CA) in HHHSA. The plate was resealed, and shaken for 30 minutes at 4° C. Cells were washed twice in HHHSA, once in PBS 5% FCS, and resuspended in 200 µl of PBS, 2.5% FCS, 1% paraformaldehyde. The samples were analyzed on an EPICS V flow cytometer.

Reagents

All chemical reagents were of highest grade and purchased from Sigma Chemical Co. (St. Louis, MO) except the following: rIL-1$\beta$ (Genentech, CA), HE (Polysciences, Warrington, PA), SFDA (Molecular Probes), $Na_2{}^{51}CrO_4$ and $Na^{125}I$ (Amersham, IL), Dextran-500 (Pharmacia, Sweden), fetal calf serum (Flow Laboratories or JR Scientific), endothelial cell growth factor (Chemicon International, Los Angeles, CA), HSA (Alpha Corporation, Los Angeles, CA), FITC goat anti mouse Ab (Zymed, CA), Protein A (Pharmacia, Sweden), Iodogen (Pierce), Triton X-100 (DuPont, Wilmington, DE), CsCl (BRL), hypoxanthine (GIBCO, NY).

EXAMPLE 2

Adhesion of Mac-1 and LFA-1 Transfectants to Purified ICAM-1

The studies of Smith, C. W., et al. (*J. Clin. Invest.* 83:2008-2017 (1989)) which suggested to the present inventors that Mac-1 on neutrophils binds to ICAM-1 are complicated by the presence of multiple adhesion receptors on neutrophils, e.g., neutrophils express significant quantities of both LFA-1 and Mac-1. The above-described methods utilized a purified protein-transfectant cell binding assay where each of the ligand pairs was examined independently for adhesion (Larson, R. S., et al., *Cell Reg.* 1:359-367 (1990), herein incorporated by reference).

COS cells co-transfected with the cDNA's for the common $\beta$ subunit and either the Mac-1 or LFA-1 $\alpha$ subunit were assayed for binding to purified ICAM-1 coated on a plastic substrate using the methods described above. Surface expression averaged 30% for ICAM-1 and 40% for LFA-1 as determined by immunofluorescence flow cytometry. Transfected COS cells expressing Mac-1 and LFA-1 bound purified ICAM-1 (FIG. 1), while cells transfected with the $\beta$ chain alone did not bind. Adhesion was specific as monoclonal antibodies to LFA-1, Mac-1 and ICAM-1 inhibited attachment, whereas a control monoclonal antibody that binds the monkey homologue of CD29 did not inhibit binding.

In FIG. 1, COS cells co-transfected with cDNAs of LFA-1 or Mac-1 $\alpha$ chains and the common $\beta$ chain were labeled with $^{51}Cr$ and then both the cells and the ICAM-1-coated substrates were pretreated with the following monoclonal antibody: control (TS2/16), LFA-1 (TS1/22), Mac-1 (LPM19c), ICAM-1 (R6.5 and RR1/1). Subsequently, the cells were allowed to settle on ICAM-1-coated 35 mm Petri dishes for 1 hour at 37° C. Plates were washed four times by pipetting and bound cells were removed and quantitated for gamma emission. Prior to $^{51}Cr$ labeling, a small percentage of the cells were stained with LFA-1 (TS1/22) or Mac-1 (LM2/1) monoclonal antibody and the percentage of positive cells was determined by flow cytometry. The data was normalized for surface expression by dividing the percentage of bound cells by the percentage of positive cells. Without normalization COS cells transfected with the $\beta$ chain alone, Mac-1, and LFA-1 were positive for expression in 7%, 30%, and 40% of the cells respectively. The data was the average of three separate experiments and the error bars represent the standard errors of the mean.

The adhesion of Mac-1 transfectants was weaker (44% binding compared to 75% for LFA-1 transfectants) and occurred at 37° C. but not at 23° C. whereas COS cells transfected with LFA-1 bound to ICAM-1 at 23° C.

EXAMPLE 3

Immunoaffinity Purification of Functional Mac-1

To gain additional evidence for an interaction between Mac-1 and ICAM-1, the above-described reciprocal assay was used to determine whether cells bearing ICAM-1 bound to purified Mac-1. Mac-1 was purified as described above using a modified form of the procedure which had been used to obtain LFA-1 in a form that was functional and in which the $\alpha$ and $\beta$ chains remained non-covalently associated (Dustin, M. L., et al., *Nature* 341:619-624 (1989)).

Peripheral blood leukocytes were lysed in Triton X-100 in the presence of $Mg^{2+}$, and the Mac-1 $\alpha/\beta$ complex was bound to an LM2/1 monoclonal antibody affinity column as described above. Triton X-100 was exchanged with the dialyzable detergent octyl-$\beta$-D- glucoside. Elution conditions of varied salt, divalent cation concentration and pH were tested and optimized for yield and the ability to reprecipitate the heterodimer. The optimum buffer contained 50 mM triethylamine pH 10.0, 300 mM NaCl, and 2 mM $Mg^{2+}$. Mac-1 obtained by this procedure was substantially pure, and migrated on reducing SDS-PAGE as two bands with $M_r$ of 160,000 and 95,000, consistent with previous observations (Miller, L. J., et al., *Immunol.* 138:2381-2383 (1987)). Immunoprecipitation with the anti-$\beta$ monoclonal antibody TS1/18 of the purified material yielded the heterodimer, indicating that the two chains, after elution, remained associated. This material had complement receptor three activity as it bound specifically to iC3b coated erythrocytes but not to erythrocytes coated only with anti-Forsmann antibody (Diamond, M. S., et al., In *Leukocyte Typing IV*, Knapp. W., et al. (eds.), Oxford University, London, pp. 570-574 (1989), herein incorporated by reference). Approximately 500 μg of intact Mac-1 was recovered from 10 g of leukocytes.

EXAMPLE 4

Adhesion of Cells Transfected with ICAM-1 cDNA to Purified Mac-1 and LFA-1

To test whether cells bearing ICAM-1 interact with Mac-1, COS cells were transfected with the ICAM-1 cDNA and allowed to settle on Mac-1 coated substrates, as described above. Surface expression of ICAM-1 on transfected COS averaged 50-60% while vector transfected COS cells showed no expression. This was determined by analyzing the fluorescence intensity of COS cells transfected with either vector alone or ICAM-1 cDNA, or with L cells, untransfected or transfected with ICAM-1 cDNA. The cells were incubated with ICAM-1 monoclonal antibody (RR1/1), FTTC goat-anti-mouse IgG and subjected to flow cytometry. COS cells expressing ICAM-1 adhered to purified Mac-1 whereas cells transfected with vector alone did not adhere. To demonstrate this, COS cells were transfected with ICAM-1 cDNA or vector alone, and were allowed to settle on a spot of purified Mac-1 in a 35 mm Petri dish for 50 minutes at 37° C. Cells and the dishes were pretreated with monoclonal antibody for 20 minutes with control (TS2/16), Mac-1 (LPM19c), or ICAM-1 (R6.5 and RR1/1). After incubation, plates are washed three times with a Pasteur pipette to remove unbound cells. The binding was specific as it was blocked completely with monoclonal antibodies to Mac-1 $\alpha$ (LPM19c) or ICAM-1 (R6.5 and RR1/1).

To assess more quantitatively the strength of the interaction between Mac-1 and ICAM-1, a dose response analysis was performed. Because of the variation between experiments in the percentage of COS cells expressing ICAM-1 and the heterogeneity in the level of ICAM-1 expression between cells, stable transfectants expressing human ICAM-1 expression between cells, stable transfectants expressing human ICAM-1 in murine L cells were generated as described by (Chen, C. A., et al., *BioTechniques* 6(7):632-637 (1988), herein incorporated by reference).

Colonies were selected in which 100% of the L cells expressed high amounts of human ICAM-1. Titration experiments were performed in which ICAM-1+ L cells were allowed to bind to substrates coated with a wide range of Mac-1 site densities (FIG. 2).

Figure 2:
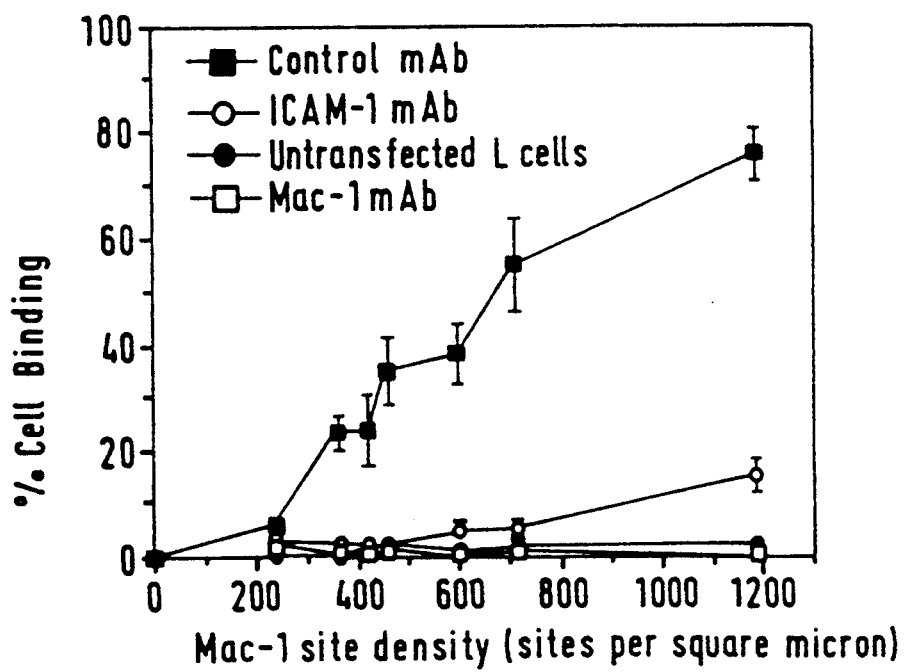
FIG. 2 shows a dose response curve of ICAM-1+ L cell adhesion to purified Mac-1.

In FIG. 2, ICAM-1 + or ICAM-1 − (untransfected) L cells are labeled With $^{51}Cr$. For antibody blocking experiments, both the 96-well plates and cells were pretreated with the following monoclonal antibody: control (M1/42), Mac-1 (LPM19c), and ICAM-1 (R6.5). Cells were added to Mac-1 coated wells and incubated 45 minutes at 37° C. Unbound cells were removed after four washes by fine needle aspiration (26 gauge). Bound cells were removed with 0.2N NaOH and quantitated by $\gamma$ emission. Site densities were determined in parallel and were quantitated by radioimmunoassay with $^{125}I$-LM2/1. All experiments were performed in triplicate and the data shown is the average of three separate experiments. The error bars represent standard deviations.

L cells expressing ICAM-1 adhered to Mac-1 in a dose dependent fashion with a threshold of approximately 250 sites/$\mu m^2$ before significant adhesion was seen. The adhesion was specific as plates pretreated with monoclonal antibody to Mac-1 $\alpha$ (LPM19c), cells pretreated with monoclonal antibodies to ICAM-1 (RR1/1 and R6.5), and untransfected L cells did not attach.

Figure 3:
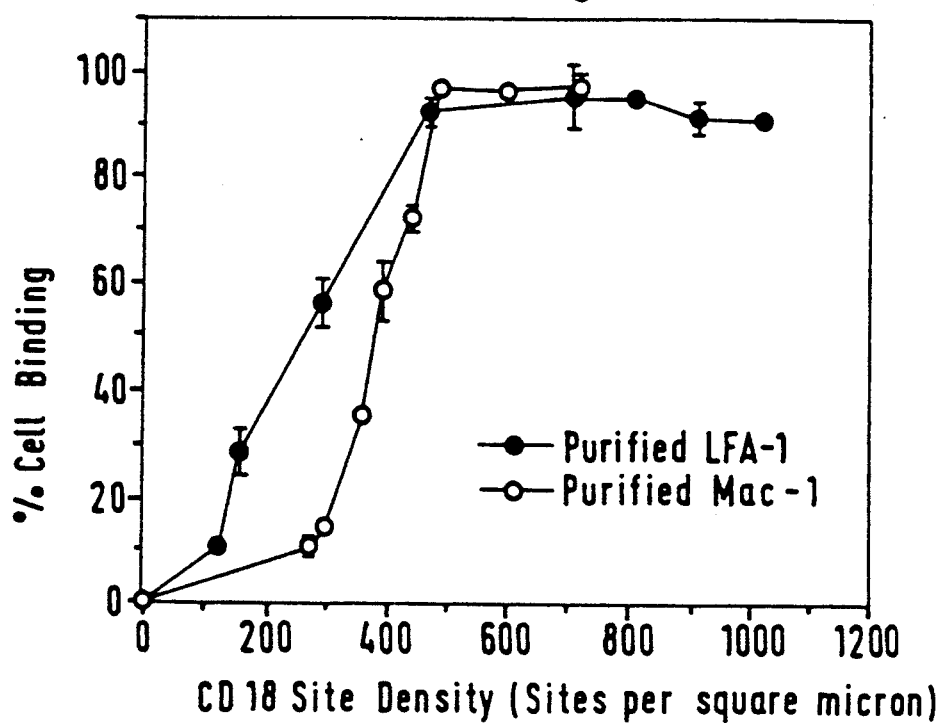
FIG. 3 shows an avidity comparison of ICAM-1+ L cells for purified Mac-1 and LFA-1.

Parallel experiments were performed on LFA-1 and Mac-1 coated substrates to determine the difference in relative avidity for using a lower stringency wash protocol (FIG. 3). The amount of Mac-1 and LFA-1 bound to substrate was determined by radioimmunoassay with a monoclonal antibody to the common $\beta$ subunit.

Percent binding was determined in the following manner: ICAM-1+ L cells were added to 60 mm Petri dishes coated with a spot of Mac-1 (FIG. 3, open circles) and LFA-1 (FIG. 3, shaded circles) for 50 minutes at 37° C. Unbound cells were removed by three washes with a Pasteur pipette. Bound cells were quantitated by visually scoring the number of cells in 4-5 high power light microscope fields for each experimental point. This number was divided into the input number of cells to obtain the percentage of cells binding. Binding outside the integrin-coated spots varied between 1-3%. Site densities were determined using $^{125}I$-TS1/18 (anti-CD18). One representative experiment of two is shown and the error bars represent standard deviations.

Figure 4:
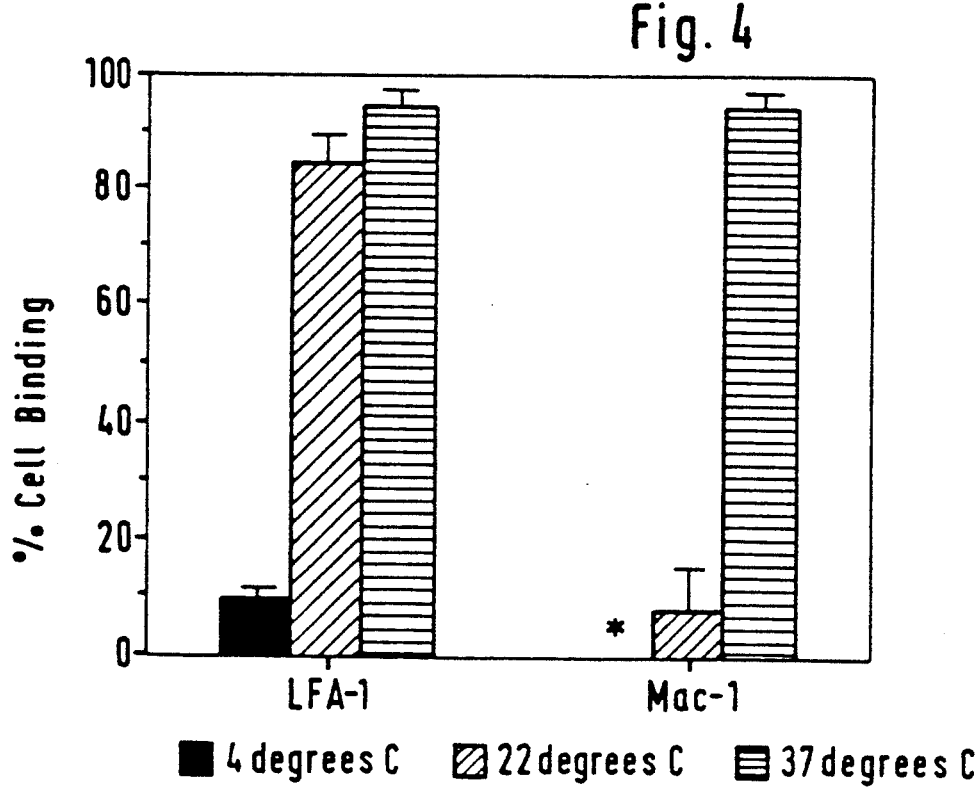
FIG. 4 shows the temperature dependence of ICAM-1+ cell adhesion to purified Mac-1 and LFA-1.

ICAM-1+ L cells adhered to LFA-1 substrates with a slightly higher avidity as the binding isotherm for purified Mac-1 was shifted to a higher site density. Binding of ICAM-1+ L cells to Mac-1 was more temperature sensitive than binding to LFA-1 (FIG. 4). In FIG. 4, ICAM-1+ L cells were preincubated at the indicated temperature for ten minutes, and then added to 60 mm Petri dishes containing spots of Mac-1 and LFA-1. The dishes were incubated at the appropriate temperature for 50 minutes, washed thrice by Pasteur pipette, and scored visually for adherent cells at high power magnification. Site density for LFA-1=803 sites/$u^2$ and Mac-1=738 sites/$u^2$ as determined by radioimmunoassay with $^{125}I$-TS1/18 (anti-CD18). The percent binding was determined as described above. In FIG. 4, one representative experiment of two is shown, the data is the average of two experiments and the error bars represent standard deviations. The asterisk indicates there was no binding of ICAM-1 transfectants at 4° C. to purified Mac-1.

Despite equivalent site densities of LFA-1 and Mac-1 on the substrate, cells adhered strongly to LFA-1 but weakly to Mac-1 at room temperature, while there was little or no difference in the quantitative adhesion at 37° C.

EXAMPLE 5

Adhesion of HUVEC to Purified Mac-1

To confirm that stimulated HUVEC adhered to Mac-1 in an ICAM-1 dependent fashion, their ability to bind Mac-1 substrates was tested. HUVEC, when stimulated for 18-24 hours with IL-1β or LPS, was found to bind to purified Mac-1 under high stringency wash conditions (FIG. 5).

Figure 5:
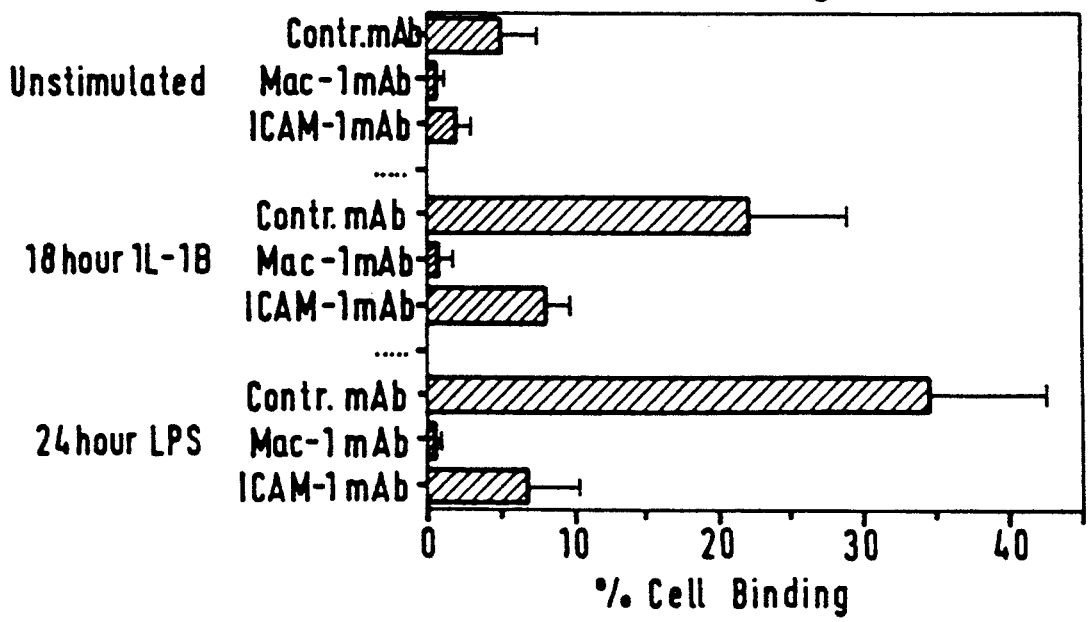
FIG. 5 shows HUVEC adhesion to purified Mac-1.

In FIG. 5, HUVEC that were unstimulated or stimulated with IL-1β (5 U/ml, 18 h) and LPS (1 μg/ml, 24 h) were labeled with $^{51}Cr$, added to Mac-1 coated 96-well plates and incubated for 1 hour. Unbound cells were washed at high stringency by fine needle aspiration; bound cells were recovered and quantitated by γ emissions. Antibody blocking was performed by preincubating the cells and the plates at room temperature for 25 minutes with the following monoclonal antibody: control (W6/32), Mac-1 (LMP19c), ICAM-1 (R6.5 and RR1/1). The experiments were performed in triplicate and the data shown is the average of three separate experiments. Error bars indicate standard deviations.

Adhesion was specific and primarily ICAM-1 dependent since it was inhibited by monoclonal antibody to ICAM-1 (82% for LPS, 66% for IL-1β) and Mac-1 α (>95% in both cases) but not by control monoclonal antibody. Unstimulated HUVEC, which expressed lower amounts of ICAM-1 (Dustin, M. L., et al., *J. Immunol.* 137:245-254 (1986)) did not attach significantly to purified Mac-1 at this stringency of wash.

EXAMPLE 6

Differences Among ICAM-1 Monoclonal Antibodies in Blocking Adhesion to Mac-1 and LFA-1

The reciprocal adhesion assays described above showed that both Mac-1 and LFA-1 were able to bind to ICAM-1. This result prompted the question of which epitopes on ICAM-1 were involved in interactions with LFA-1 and Mac-1. To address this question, ICAM-1+ L cell ICAM-1 was examined as a ligand for Mac-1.

To do this, ICAM-1+ L cells were pretreated with saturating concentrations of the indicated ICAM-1 monoclonal antibody for 20 minutes at 4° C. Cells were then added to a 60 mm Petri dish spotted with Mac-1 or LFA-1, and incubated for 50 minutes at 37° C. Unbound cells were removed with three washings using a Pasteur pipette. The percentage of bound cells were determined as described above (FIG. 6). The data is the mean of two separate experiments and error bars show standard deviation.

Monoclonal antibody blocking data (FIG. 6) suggests differences with respect to the site of interaction on ICAM-1 for LFA-1 and Mac-1. Only one monoclonal antibody (R6.5) was able to significantly inhibit binding of ICAM-1 transfected L cells to substrates coated with Mac-1 and LFA-1 whereas others (RR1/1, LB-2, 84H10, CBRIC1/4) that block LFA-1-ICAM-1 function (Lo, S. K. et al., *J. Immunol.* 143:3325-3329 (1989); Makgoba, M. W. et al., *Nature* 331:86-88 (1988); Marlin, S. D., *Cell* 51:813-819 (1987); Rothlein, R. et al., *J. Immunol.* 137:1270-1274 (1986); Smith, C. W., et al., *J. Clin. Invest.* 82:1746-1756 (1988)) did not decrease binding to Mac-1.

Furthermore, one new monoclonal antibody (CBRIC1/1) partially blocked Mac-1-ICAM-1 adhesion.

Additional evidence indicates that Mac-1 and LFA-1 do not interact identically with ICAM-1. Larson et al. (*Cell Reg.* 1:359-367 (1990), herein incorporated by reference) has shown that when Mac-1 and LFA-1 expressing COS cell transfections are allowed to adhere to ICAM-1 coated substrates and washed under high stringency conditions by fine needle aspiration (Dustin, M. L., et al., *Nature* 341:619-624 (1989)), only LFA-1+ cells remain attached. However, the experiments described herein reveal that if the cells are washed more gently, both Mac-1 and LFA-1 transfected COS cells remained bound. Thus, the LFA-1 ICAM-1 interaction appears more shear-resistant. This phenomenon can be explained, in part, by a difference in the avidity of the binding. When parallel adhesion assays are performed with ICAM-1+ L cells binding to either Mac-1 or LFA-1, a lesser amount of LFA-1 than Mac-1 is found to sustain cell adhesion. A caveat is that although a monoclonal antibody to the common β subunit is used to quantitate Mac-1 and LFA-1 density, and the monoclonal antibody reacts with associated but not free β subunit (Kishimoto, T. K., et al., *Cell* 50:193-202 (1987)), the percentage of protein that is on the plastic is in an active conformation that can bind to ICAM-1 is not ascertained.

EXAMPLE 7

Effect of Chemotactic Stimulation of Neutrophils on Conjugation with HUVEC

Chemotactic stimulation of neutrophils resulted in a significant increase in conjugation with HUVEC over the baseline conjugate formation of unstimulated neutrophils (Table 2). There was a three-four fold increase in the number of HUVEC conjugated with neutrophils after stimulation. When TS1/22, an anti-LFA-1 α monoclonal antibody was added, there was a slight but not statistically significant inhibition of conjugate formation. If monoclonal antibody to the Mac-1 α monoclonal antibody was added, there was a significant inhibition (73%) of stimulated cell conjugates. A combination of anti-LFA-1 and anti-Mac-1 monoclonal antibodies or an antibody against the common β chain showed the greatest inhibition (88%-98%). R6.5 Fab and RR1/1 Fab$_2$ fragments decreased conjugate formation by 48.3%. Since this inhibition was greater than that of LFA-1 antibodies alone, the results indicate that both LFA-1 and Mac-1 interacted with ICAM-1. Because the CD18 dependent adhesion could not be inhibited solely with monoclonal antibodies to ICAM-1, LFA-1 and/or Mac-1 appeared to be interacting with additional ligands. For LFA-1, ICAM-2 is a strong possibility, yet it does not appear that Mac-1 binds to ICAM-2 and thus, other endothelial cell surface counter-receptor(s) may be involved.

In Table 2, neutrophils ($1.5 \times 10^6$) stained red with HE and HUVEC ($6 \times 10^5$) stained green with SFDA were resuspended and pretreated separately with the following monoclonal antibody: Control (W6/32), ICAM-2 (CBRIC2/1); LFA-1 (TS1/22), Mac-1 (LPM19c), CD18 (YFC51.1), ICAM-1 (R6.5 Fab and RR1/1 Fab'$_2$). The cells were mixed in 24 well plates and preincubated at 37° C. fMLP ($10^{-7}$ M) was added and the cells were agitated at 75 rpm for ten minutes at 37° C. Resultant suspensions were analyzed immediately by flow cytometry. The data is expressed as the percentage of HUVEC found in heterotypic conjugates with neutrophils, and the inhibition of conjugation of stimulated neutrophils is expressed relative to the baseline level of conjugates without stimulation with fMLP. Significance values were determined using a pooled T-test. NS means that values were statistically different (p>0.05) from controls. Values in parentheses how standard deviations.

TABLE 2

Conjugate Formation between fMLP Stimulated Neutrophils and 24-hour LPS Cultured HUVEC

| Monoclonal Antibody | fMLP | % HUVEC in Conjugates | n | % Inhibition of Adherence |
|---|---|---|---|---|
| None | — | 12 ± 3 | 6 | — |
| CD18 | — | 9 ± 1 | 3 | 25.0 NS |
| None | + | 42 ± 6 | 5 | — |
| Control | + | 41 ± 5 | 7 | 0.3 NS |
| ICAM-2 | + | 44 ± 6 | 5 | 0.6 NS |
| LFA-1 | + | 38 ± 6 | 5 | 14.4 NS |
| Mac-1 | + | 21 ± 6 | 7 | 73.0 ($p < 0.005$) |
| CD18 | + | 16 ± 5 | 5 | 88.0 ($p < 0.0005$) |
| Mac-1 + LFA-1 | + | 13 ± 3 | 5 | 98.3 ($p < 0.0005$) |
| ICAM-1 | + | 27 ± 3 | 8 | 48.3 ($p < 0.0005$) |

EXAMPLE 8

Conclusions Regarding The Interaction Between Mac-1 and ICAM-1

The above-described experiments prove that Mac-1, like LFA-1 (Marlin, S. D., Cell 51:813-819 (1987)), is a Counter receptor for ICAM-1 by demonstrating that purified Mac-1 mediated cell adhesion dependent on ICAM-1, and reciprocally that purified ICAM-1 mediated cell adhesion dependent on Mac-1.

Cells transfected with specific cDNA's of putative counter receptors were used to eliminate complications associated with additional receptor-ligand interactions. The results show that ICAM-1+ transfectants and Mac-1+ transfectants bind purified Mac-1 and ICAM-1, respectively. To rule out the possibility that these results were an artifact of the experimental system, a Mac-1, ICAM-1 dependent adhesion between stimulated endothelial cells and purified Mac-1 was demonstrated.

A Mac-1 - ICAM-1 interaction in a cell-cell context was also shown since stimulated Mac-1+ peripheral blood neutrophils from cell conjugated with ICAM-1+ HUVEC in a manner that was inhibited with Mac-1 and ICAM-1 monoclonal antibodies.

The binding of ICAM-1 to both Mac-1 and LFA-1 showed that an immunoglobulin-like molecule could adhere to more than one integrin. However, the interaction between the two sister leukocyte integrins and ICAM-1 is not identical.

Another feature distinguishing the interaction with LFA-1 and Mac-1 is the striking effect of temperature on adhesion. While ICAM-1+ L and COS cells bind strongly to purified solid phase LFA-1 at room temperature (FIG. 4), there is a strict 37° C. temperature requirement for significant adhesion to purified Mac-1 (FIG. 4). Interaction of ICAM-1 bearing cells with purified Mac-1 also appears more energy-dependent than interaction with LFA-1 (Staunton, D. E., Nature 339:61-64 (1989)). The temperature and energy dependence of Mac-I ICAM-1 interaction may be due to a requirement for greater ICAM-1 clustering on the cell surface or to a need for closer cell-substrate apposition. Consistent with the stronger interaction with LFA-1, it is observed that transfected cells expressing ICAM-1 spread and flatten out more on LFA-1 coated substrates than on Mac-1 substrates.

The binding of Mac-1 to ICAM-1 demonstrates directly that Mac-1 interacts with an endothelial cell surface counter-receptor. This finding explains previous studies which show that neutrophil adhesion to endothelial cells is inhibited by monoclonal antibody to Mac-1 (Anderson, D. C., et al., J. Immunol. 137:15-27 (1986); Harlan, J. M., et al., Blood 66:167-178 (1985); Zimmerman, G. A., et al., J. Clin. Invest. 81:531-537 (1988)) and that Mac-1 and LFA-1 dependent adhesion of fMLP-stimulated neutrophils to unstimulated endothelial cells (Smith, C. W., et al., J. Clin. Invest. 82:1746-1756 (1988)) or ICAM-1 containing planar membranes (Smith, C. W., et al., J. Clin. Invest. 83:2008-2017 (1989)) is blocked completely by a monoclonal antibody to ICAM-1 (R6.5).

In contrast, ICAM-1 has been reported not to be a ligand for Mac-1 (Lo, S. K., et al., J. Immunol. 143(10):3325-3329 (1989)). In that study, neutrophils stimulated with phorbol esters adhere to unstimulated endothelial cells in manner that is LFA-1, Mac-1 and ICAM-1 dependent, results that agree with the data presented herein. However, this group concluded that only LFA-1 interacts with ICAM-1 because the inhibition with LFA-1 and ICAM-1 monoclonal antibodies (LB-2, 84H10) was not additive whereas the inhibition with Mac-1 and ICAM-1 monoclonal antibodies was additive. The differences in the previous reports may be explained partially by the disparity in monoclonal antibody selection; here, it is shown that R6.5 monoclonal antibody blocked both Mac-1 and LFA-1-ICAM-1 interactions whereas LB2 and 84H10 monoclonal antibody only inhibit LFA-1-ICAM-1 binding (FIG. 6).

The monoclonal antibody blocking data presented herein is consistent with mutagenesis studies that map mAb epitopes to distinct regions of the ICAM-1 molecule (Staunton, D. E., et al., Cell 61:243-254 (1990)). RR1/1 and LB-2 map to the first N-terminal immunoglobulin domain whereas R6.5 maps to the second domain. The data is also consistent with in vivo experiments (Barton, R. W., et al., J. Immunol. 143:1278-1282 (1989)) that show a reduction in the granulocyte infiltration into rabbit lungs inflamed with phorbol esters after pretreatment with monoclonal antibodies to CD18 (R3.3) or ICAM-1 (R6.5), but not with monoclonal antibody to LFA-1 (R3.1). These findings indicate that stimulated neutrophils may utilize a Mac-1-ICAM-1 dependent pathway of adhesion to mediate attachment in vivo to inflamed endothelium.

Experiments presented here are consistent with the possibility of counterreceptors for Mac-1 distinct from ICAM-1 on the surface of unstimulated (Lo, S. K., et al., J. Immunol. 143(10):3325-3329 (1989)) and stimulated enthothelial cells. In the assays used herein, endothelial cell ICAM-1 cannot by itself account for all of the Mac-1 dependent adhesion of neutrophils. Adhesion of stimulated HUVEC to purified Mac-1 under high stringency wash conditions was only partially (66-82%) blocked by monoclonal antibody to ICAM-1 (FIG. 5). Furthermore, there was little adhesion of unstimulated HUVEC to Mac-1 at this stringency, but when washed at a lower stringency, there was significant non-ICAM-1 dependent adhesion to purified MAC-1. This result conflicts with a report that showed that fMLP stimulated neutrophil adhesion to unstimulated endothelial cells was blocked 84% by a monoclonal antibody to ICAM-1 (Smith, C. W., et al., *J. Clin. Invest.* 82:1746-1756 (1988)). This discrepancy may be explained by differences in tissue culture conditions of untreated HUVEC which may induce a second ligand for Mac-1.

Thus, the present invention describes the use of multiple cell binding assays, purified Mac-1 and ICAM-1, and cell lines transfected with Mac-1 and ICAM-1 cDNAs to examine the interaction of ICAM-1 with Mac-1. Stimulated HUVEC, which express a high surface density of ICAM-1, bind to immunoaffinity purified Mac-1 adsorbed to artificial substrates in a manner that was found to be inhibited by monoclonal antibodies to Mac-1 and ICAM-1. Transfected murine L cells or monkey COS cells expressing human ICAM-1 bound to purified Mac-1 in a specific and dose-dependent manner; the attachment to Mac-1 was found to be more temperature sensitive, lower in avidity, and blocked by a different series of ICAM-1 monoclonal antibodies when compared to LFA-1. In a reciprocal assay, COS cells cotransfected with the α and β chain cDNAs of Mac-1 or LFA-1 attached to immunoaffinity purified ICAM-1 substrates; this adhesion was blocked by monoclonal antibodies to ICAM-1 and Mac-1 or LFA-1. Two color fluorescence cell conjugate experiments showed that neutrophils stimulated with fMLP bound to HUVEC stimulated with LPS for 24 hours in an ICAM-1, Mac-1, and LFA-1-dependent fashion. Because cellular and purified Mac-1 interacted with cellular and purified ICAM-1, it was concluded that ICAM-1 is a counterreceptor for Mac-1 and that this receptor is responsible, in part, for the adhesion between stimulated neutrophils and stimulated endothelial cells.

The above-described studies show that ICAM-1 is a counter receptor, not only for LFA-1, but also for Mac-1. The cell-cell binding studies demonstrate that neutrophil Mac-1 interacts with ICAM-1 expressed on HUVEC These findings also indicate that Mac-1 interacts with at least one additional cellular ligand, besides ICAM-1, on the surface of endothelial cells.

EXAMPLE 9

Mapping of the Mac-1 Binding Site

Unexpectedly, the monoclonal antibody blocking data presented above, suggested that Mac-1 and LFA-1 did not share the same binding site on ICAM-1. To investigate this issue, amino acid substitution and domain deletion mutagenesis of ICAM-1 were performed.

Oligonucleotide directed mutagenesis was performed as described by Kunkel, T. A. (*Proc. Natl Acad. Sci. USA,* 82:488-492, (1985)), as modified by Peterson et al. (*Nature,* 329:842-846 (1987)), was used to generate ICAM-1 deletion substitutions (Staunton, D. E., et al., *Cell* 61:243-254 (1990), herein incorporated by reference).

COS cells at 50% confluency were transfected by the DEAE-dextran method (Kingston, R. E., In *Current Protocols in Molecular Biology,* Greene Publishing Associates, pp. 9.0.1-9.9.6 (1987)) using 6 μg of vector alone or vector containing the wild type or mutated form of ICAM-1. COS cells were suspended using trypsin-EDTA 1 day before assay (Day 3 and reseeded. For assays of binding to purified Mac-1 or LFA-1 or immunofluorescence staining, the transfected cells eluted with phosphate buffered saline (PBS), 5 mM EDTA (5 minutes, 37° C.), and washed thrice in PBS, 1 mM MgCl$_2$, 0.5 nM CaCl$_2$, 0.2% glucose, 0.25% human serum albumin.

Indirect immunofluorescence staining was performed using the monoclonal antibodies RR1/1 (Rothlein, R. M., et al., *J. Immunol.* 137:1270-1274 (1986)), R6.5 (Rothlein et al., *J. Immunol.,* 141:1665-1669, (1988)), and CL203 (Maio, M., et al., *J. Imunol.* 143:181-188 (1989)). COS cells (5×10$^5$) were added to 50 mm Petri dishes coated with demarcated spots of immunoaffinity purified Mac-1 and LFA-1 and allowed to adhere for 45 minutes at 37° C. Unbound cells were removed with four washes with a transfer pipette, the plates were coded, and bound cells were counted by three independent observers. Binding of ICAM-1 mutants to LFA-1 and Mac-1 was corrected for binding to COS cells transfected with vector without insert (mock) and was normalized to the percentage of COS cells staining with the monoclonal antibody RR1/1 or CL203 (depending on the deletion) and for the percentage of binding obtained in the wild type:

$$\% \text{ binding} = \frac{\frac{\% \text{ mutant binding} - \% \text{ mock binding}}{\% \text{ mutant monoclonal antibody staining}}}{\frac{\% \text{ wild type binding} - \% \text{ mock binding}}{\% \text{ wild type monoclonal antibody staining}}} \times 100$$

To show the effect of amino acid substitutions on ICAM-1 binding to LFA-1 and Mac-1, such mutants were constructed as described Staunton, D. E., et al., *Cell* 61:243-254 (1990). The binding assay, immunofluorescence, and data reduction were performed as described in FIG. 7. Mutants that are italicized and underscored to not express all of the epitopes of monoclonal antibodies in domains 1 and 2 Staunton, D. E., et al., *Cell* 61:243-254 (1990). Boldface mutants in domain 1 correspond to those which decrease binding to LFA-1 greater than 75%. Boldface mutants in domain 3 correspond to those which have a significant effect on binding to Mac-1 ($p<0.05$).

Figure 8:
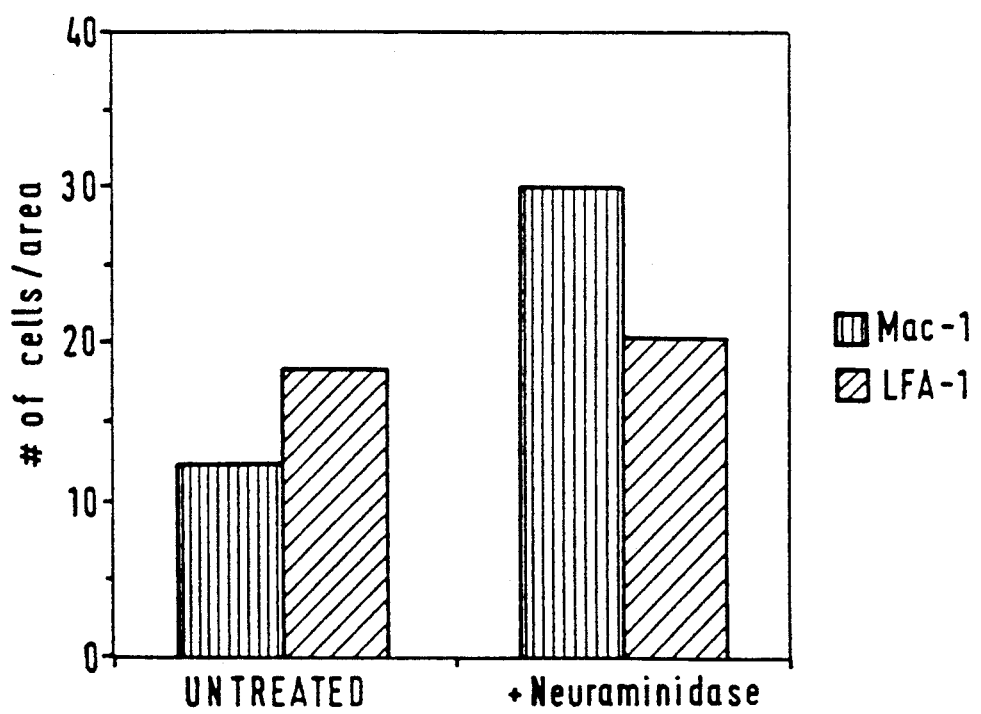
FIG. 8 shows the effect of the endoplasmic reticulum glucosidase inhibitor deoxymannojirimycin on adhesion of ICAM-1+ cells to Mac-1.

The endoplasmic reticulum glucosidase inhibitor, deoxymannojirimycin was tested for its effect on ICAM-1+ L and COS cell adhesion to purified Mac-1 (FIG. 8). This inhibitor blocks complex carbohydrate addition in the golgi apparatus, and thus proteins with N-linked sites retain a high mannose, Endo H-sensitive glycosylation. Cells were treated with 40 μg/ml deoxymannojirimycin (CalBiochem) for three days, and then assayed for surface expression by flow cytometry and for adhesion.

EXAMPLE 10

The Mac-1 Binding Site of ICAM-1

In the transfectant experiments described above, it was unexpectedly observed that the pattern of inhibition among monoclonal antibody to ICAM-1 differs between LFA-1 and Mac-1; four monoclonal antibodies to ICAM-1 that blocked LFA-1-ICAM-1 interaction did not affect binding to Mac-1, one monoclonal antibody which reduced adherence to Mac-1 did not decrease attachment to LFA-1, and only one monoclonal antibody blocked adhesion to both Mac-1 and LFA-1.

Previously, the ICAM-1 binding for LFA-1 has been localized to the first two N-terminal Ig-like domains using domain deleted forms of ICAM-1. In the experiments reported herein, the binding site on ICAM-1 for Mac-1 has been localized. Table 3 shows the binding of amino acid substitution mutants to LFA-1 and Mac-1. The data is the average of 2-3 independent experiments and the values in parentheses represent standard deviations.

Figure 7:
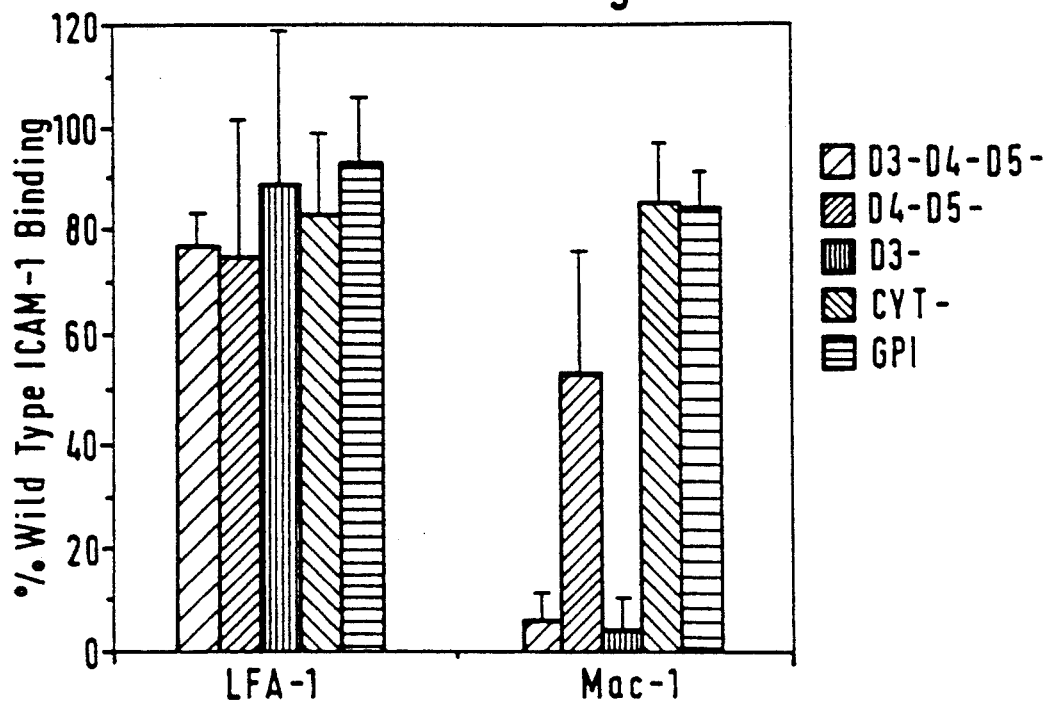
FIG. 7 shows the binding of domain deletion mutants of ICAM-1 to LFA-1 and Mac-1. The data is the average of three independent experiments and the error bars represent standard deviations.

To identify the binding site, domain deleted forms of ICAM-1 that were generated by oligonucleotide-directed mutagenesis (Staunton, D. E., et al., Cell 52:925-933 (1988)) were transfected into COS cells, assayed for positive expression by immunofluorescence, and tested for adherence to demarcated spots of purified Mac-1 and LFA-1 (FIG. 7).

This confirmed that the ability to bind to purified LFA-1 is retained after the deletion of Ig-like domains D3-D5 or deletion of the cytoplasmic tail. However, the results for Mac-1 were quite different. Adhesion to Mac-1 was retained only if D3 is present. Both the D3-D4-D5- and the D3- mutants lost their ability (>95%) to bind purified Mac-1. Loss of the cytoplasmic domain or placement of the five extracellular Ig-like domains of ICAM-1 on a phosphoinositolglycan tail had no significant effect on adhesion to Mac-1, and deletion of D4 and D5 decreased binding to Mac-1 only to a small extent.

To confirm that D1 of ICAM-1 was not required for interaction with Mac-1, amino acid substitution mutants of ICAM-1 (Staunton, D. E., et al., Cell 61:243-254 (1990)) were tested for their ability to adhere to Mac-1. These mutants were made in the loops that connect the β-strands according to structural predictions of Ig-like molecules; it is hypothesized that the loops function as the site of intermolecular contact in members of the Ig superfamily (Williams et al., Ann. Rev. Immunol., 6:381-405 (1988)). The two single amino acid substitution mutants in D1 that most strongly abrogate binding to LFA-1 without altering domain conformation, E34/A and Q73/H, do not decrease adhesion to purified Mac-1 (Table 3). Three other mutants, R13G/EA, Q58EDS/AKDI, and D60S/KL, which disrupted the conformation of D1 and D2, as judged by loss of three distinct monoclonal antibody epitopes (Staunton, D. E., et al., Cell 52:925-933 (1988)), all abolished binding to LFA-1 but had no effect on binding to Mac-1. All other mutants in D1 had no effect on ICAM-1 adhesion to Mac-1. This data indicates that D1 has little role in adhesion to Mac-1 and explains why monoclonal antibodies which map to D1 on ICAM-1 ((RR1/1, LB-2, 84H10) Staunton, D. E., et al., Cell 61:243-254 (1990) herein incorporated by reference) do not block wild type ICAM-1 binding to Mac-1, although to varying degrees, they reduce adhesion to LFA-1 (Staunton, D. E., et al., Cell 61:243-254 (1990)).

It has been shown that the R6.5 monoclonal antibody to ICAM-1, which recognizes an epitope in D2 (Staunton, D. E., et al., Cell 61:243-254 (1990)), reduces adhesion of wild type ICAM-1 adhesion to Mac-1 by approximately 90%. However, D2 on ICAM-1 is probably does not constitutes a major site for adhesion to Mac-1. The N103/K mutant, which thoroughly disrupted the conformation of D1 and D2 to cause significant decreases in RR1/1, LB-2, and R6.5 binding (Staunton, D. E., et al., Cell 61:243-254 (1990)), had no effect on binding to Mac-1 despite eliminating binding to LFA-1. The E111GGA/KAGS mutant which knocks out the R6.5 epitope completely, also does not reduce adhesion to Mac-1. All other amino acid substitution mutants in D2 caused no significant changes in adhesion to either Mac-1 or LFA-1 (Table 3).

The domain deletion experiments indicate that D3 is required for ICAM-1 binding to Mac-1. To confirm and extend this finding, amino acid substitution mutants in D3 were tested for their effect on adhesion to Mac-1. Three mutants had dramatic effects on adhesion to Mac-1. D229QR/HLE completely eliminated binding to Mac-1 while E254DE/KEK decreased it approximately four fold. This effect was not caused by low surface levels as both D229QR/HLE and E254DE/KEK are expressed at wild type levels (Staunton, D. E., et al., Cell 61:243-254 (1990)), and binding to LFA-1 is retained. Unexpectedly, N240DS/KNA and N269QSQE/IQAEQ, mutants which remove potential N-linked glycosylation sites, increased binding. A caveat to the D3 mutations is that because we lack more than one monoclonal antibody whose epitope maps here, we cannot be certain that some of these mutations do not disrupt grossly the conformation of the molecule. However, all mutations in D3 support adhesion to LFA-1 and the one monoclonal antibody which maps partially to D3, CBRIC1/1, maintains its epitope on ICAM-1 molecules with mutations in D229, E254, and N269.

A comparison was made between the mutations that block binding to LFA-1 and those that inhibit binding to Mac-1. The E34/A and D229 QR/HLE mutants made changes in analogous locations in the Ig-like domains of D1 and D3, in the loop between β-strands C and D (Williams et al., Ann. Rev. Immunol., 6:381-405 (1988)). In the first domain of either human ICAM-1, murine ICAM-1 (Horley et al., EMBO J., 8:1889-2896 (1989)), and human ICAM-2 there is a strong conservation in peptide sequence near the E34 residue that is proposed as a contact site between LFA-1 and ICAM-1 (Staunton, D. E., et al., Cell 61:243-254 (1990)). This critical residue in D1 aligns with the conserved Q230 (between human and mouse ICAM-1) residue in D3 that is part of the mutation D229QR/HLE which abolishes binding to Mac-1.

The mutations, N240DS/KNA and N269QSQE/IQAEQ, enhanced ICAM-1 adhesion to Mac-1 two to five fold. These effects occurred exclusively with Mac-1 and no mutation made, as yet, increased adhesion to LFA-1. The NDS and NQS peptides are two of eight consensus sequences for N-linked glycosylation in ICAM-1 (Staunton, D. E., et al., Cell 52:925-933 (1988)); these sequences all occur between D2 and D5. ICAM-1 is known to be heavily glycosylated (Dustin et al., J. Immunol., 137:256-254 (1986)) and at least seven sites have been demonstrated by enzymatic digestion with N-glycanase (Tomassini et al., J. Biol. Chem., 264(3):1656-1662 (1989)). The N240 and N269 glycosylation sites, according to structural predictions, face the same β-sheet as D229 and E254, and a bulky or heavily charged sugar group may sterically inhibit or chemically repel binding of Mac-1.

Figure 9:
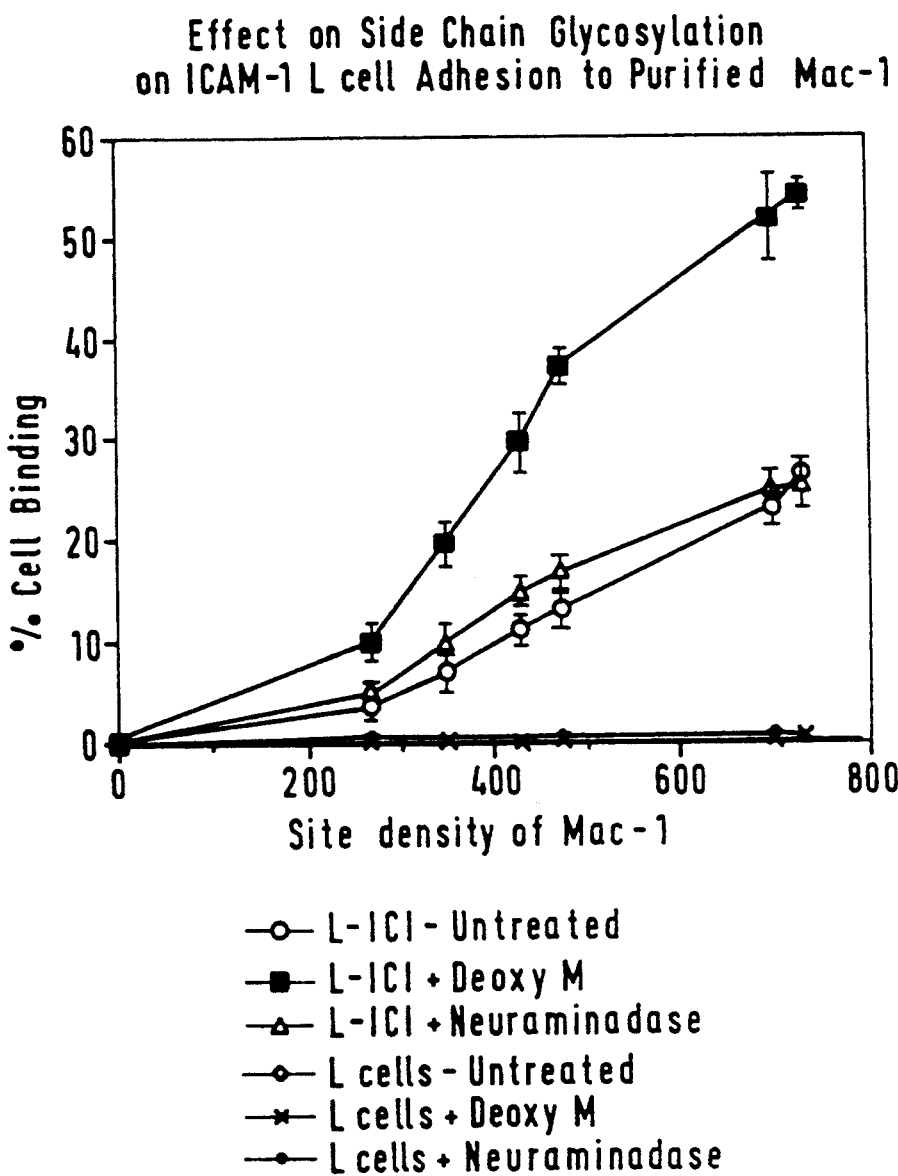
FIG. 9 shows the effect of side claim glycosylation on ICAM-1 L cell adhesion to purified Mac-1.

Because these two mutations in ICAM-1 (N240DS/KNA and N269QSQE/IQAEQ), which knock out potential N-linked glycosylation sites, also enhance binding of COS cells to purified Mac-1, we hypothesized that the extent of glycosylation on ICAM-1 may regulate adhesion to Mac-1. To test this we examined the ability of one inhibitor of glycolytic processing deoxymannojirimycin, and one deglycosylation enzyme, neuraminidase to alter adhesion of ICAM-1 expressing L cells to purified Mac-1 (FIG. 9). Deoxymannojirimycin inhibits the Golgi associated enzyme mannosidase I and prevents the processing of high mannose to complex type oligosaccharides in cultured cells (Fuhrman et al., Nature 307:755-758 (1984)). Neuraminidase cleaves the terminal sialic residues on N- and O-linked carbohydrates. As shown, L cells bearing ICAM-1 that are treated for three days with deoxymannojirimycin exhibit enhanced binding to purified Mac-1 compared to untreated or neuraminidase treated cells bearing ICAM-1. Control, untransfected L cells show no change in binding with the inhibitor or enzymatic treatment. We conclude that modification of side chains in the Golgi (conversion from high mannose to complex type sugars) can alter the interaction of ICAM-1 with Mac-1.

The domain deletion and amino acid substitution experiments presented here indicate that LFA-1 and Mac-1 bind to ICAM-1 in discrete, non-overlapping regions, to sites in D1 and D3 respectively. These binding sites may have evolved as a result of duplication of tandem Ig-like domains. Sequence comparisons show that D1 and D2 of ICAM-1 as a unit had more homology to D3 and D4 of ICAM-1 or to D1 and D2 of ICAM-2 than to the individual domains within a tandem pair (D1 vs. D2 or D1 vs D4). This phenomena of tandem domain duplication is common among Ig family members (such as for NCAM and VCAM-1) although the explanation has not been clear. Ig superfamily members have been thought of generally as having one binding site, usually near the $NH_2$-terminal, which interacts with a single ligand. The present results show that additional Ig-like domains are capable of functioning; thus, tandem domain duplication may be an evolutionary mechanism that leads to additional binding sites, and in ICAM-1, these sites have diverged enough to specialize to bind distinct integrins.

Since the mutagenesis and monoclonal antibody blocking data strongly suggest that Mac-1 and LFA-1 bind to ICAM-1 in disparate regions of the molecule, an LFA-1 and a Mac-1 molecule on the same cell surface may be able to bind a single ICAM-1 molecule. Such binding would be consistent with the observed cooperation of Mac-1 and LFA-1 on neutrophils in their adhesive interactions with endothelial cell ICAM-1 (Smith, C. W., et al., *J. Clin. Invest.* 83:2008–2017 (1989), herein incorporated by reference. Such a mechanism of two related integrins binding to the same counter-structure simultaneously could apply more generally, for example, to fibronectin and its interaction with members of the VLA subfamily: VLA-4 binds to the CS-1 fragment whereas VLA-5 attaches to the RGD sequence in the 80 kd cell binding fragment (Hemler, M. E., *Ann. Rev. Immunol.*, 8:365–400, (1990)).

TABLE 3

SUMMARY OF ADHESION TO PURIFIED Mac-1 AND LFA-1 OF ICAM-1 AMINO ACID SUBSTITUTION MUTANTS

| Mutant | Mean (SD) Mac-1 | Mean (SD) LFA-1 |
| --- | --- | --- |
| (b) Domain 1 | | |
| Q1/T | 121 (80) | 150 (42) |
| K8/E | 110 (59) | 126 (33) |
| R13G/EA | 109 (19) | 3 (2) |
| D26QPK/ALPE | 99 (24) | 80 (52) |
| E34/A | 113 (14) | 1 (0) |
| K39KE/ERQ | 73 (50) | 46 (33) |
| G46NN/ASI | 101 (60) | 140 (51) |
| R49KV/EKL | 105 (45) | 115 (11) |
| O58EDS/AKDI | 75 (18) | 3 (4) |
| D60S/KL | 108 (25) | 0 (0) |
| Q52PM/API | 110 (1) | 164 (19) |
| D71/N | 75 (12) | 97 (35) |
| Q73/H | 125 (59) | 21 (19) |
| (c) Domain 2 | | |
| G101K/AN | 121 (30) | 96 (23) |
| N103/K | 110 | 0 |
| E111GGA/KAGS | 98 (16) | 84 |
| N118/Q | 122 (41) | 164 (21) |
| R125/E | 83 (37) | 101 (41) |
| E127/R | 88 (7) | 109 (34) |
| K128/R | 112 (36) | 110 (12) |
| R149RD/EEG | 102 (50) | 130 (5) |
| H152HGA/EEGS | 94 (41) | 104 (42) |
| N156/E | 124 (4) | 150 (21) |
| R166PQ/EPA | 94 (5) | 82 (37) |
| N175/A | 78 (41) | 107 (35) |
| (d) Domain 3 | | |
| A189T/SI | 162 (61) | 160 (22) |
| D203TQ/TAD | 139 (33) | 110 (14) |
| D213GL/HGV | 122 (1) | 145 (26) |
| D229QR/HLE | 1 (2) | 103 (19) |
| N240DS/KNA | 205 (137) | 144 (24) |
| E254DE/KEK | 26 (23) | 144 (24) |
| N269QSQI/IQAE | 479 (245) | 108 (32) |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An ICAM-1 functional derivative which is substantially incapable of binding to MAC-1 but is substantially capable of binding to LFA-1, wherein said functional derivative comprises domains 1-3 of ICAM-1 and said functional derivative further contains a substitution or deletion of one or more of the amino acid residues from about residues 229 to 231 and from about 254 to 256 within domain 3 of ICAM-1 or an insertion of one or more amino acid residues within the region from about residues 229 to 231 and from about 254 to 256 within domain 3 of ICAM-1.

2. The ICAM-1 functional derivative of claim 1 wherein said functional derivative is a soluble derivative of ICAM-1.

3. The functional derivative of ICAM-1 of claims 1 or 2 wherein said functional derivative of ICAM-1 further comprises domain 4 of ICAM-1.

4. The functional derivative of ICAM-1 of claims 1 or 2, wherein said substitution is selected from the group consisting of D229QR/HLE and E254DE/KEK.

5. The functional derivative of ICAM-1 of claims 1 or 2 wherein said functional derivative of ICAM-1 further comprises domains 4 and 5 of ICAM-1.

* * * * *

UNITED STATES PATENT AND TRADEMARK OFFICE
CERTIFICATE OF CORRECTION

PATENT NO. : 5,288,854

DATED : February 22, 1994

INVENTOR(S) : Diamond *et al.*

It is certified that error appears in the above-indentified patent and that said Letters Patent is hereby corrected as shown below:

Column 42, line 35, please delete "N269QSQI/IQAE" and substitute therefor --N269QSQE/IQAEQ--.

Signed and Sealed this

Seventeenth Day of September, 1996

Attest:

BRUCE LEHMAN

Attesting Officer      Commissioner of Patents and Trademarks